US012699449B2

(12) United States Patent
Yokoi et al.

(10) Patent No.: US 12,699,449 B2
(45) Date of Patent: Aug. 4, 2026

(54) RECORDING MEDIUM STORING CONVERSION PROGRAM AND CONVERSION DEVICE

(71) Applicant: THE UNIVERSITY OF ELECTRO-COMMUNICATIONS, Tokyo (JP)

(72) Inventors: Hiroshi Yokoi, Tokyo (JP); Yuankang Shi, Tokyo (JP); Shota Togo, Tokyo (JP); Yinlai Jiang, Tokyo (JP); Yusuke Yamanoi, Tokyo (JP)

(73) Assignee: THE UNIVERSITY OF ELECTRO-COMMUNICATIONS, Tokyo (JP)

( * ) Notice: Subject to any disclaimer, the term of this patent is extended or adjusted under 35 U.S.C. 154(b) by 1063 days.

(21) Appl. No.: 17/859,037

(22) Filed: Jul. 7, 2022

(65) Prior Publication Data

US 2022/0342483 A1     Oct. 27, 2022

Related U.S. Application Data

(63) Continuation of application No. PCT/JP2021/000577, filed on Jan. 8, 2021.

(30) Foreign Application Priority Data

Jan. 10, 2020     (JP) ................................. 2020-002645

(51) Int. Cl.
*A61F 2/72*          (2006.01)
*A61B 5/00*          (2006.01)
          (Continued)

(52) U.S. Cl.
CPC ............ *G06F 3/015* (2013.01); *A61B 5/7264* (2013.01); *A61F 2/72* (2013.01); *A61F 2002/704* (2013.01)

(58) Field of Classification Search
None
See application file for complete search history.

(56)               References Cited

U.S. PATENT DOCUMENTS

2009/0270754 A1     10/2009   Moridaira

FOREIGN PATENT DOCUMENTS

JP          2001-331250 A      11/2001
JP          2009-265876 A      11/2009
                (Continued)

OTHER PUBLICATIONS

English translation of the International Search Report ("ISR") of PCT/JP2021/000577 mailed on Feb. 16, 2021.

*Primary Examiner* — David H Willse
(74) *Attorney, Agent, or Firm* — METROLEX IP LAW GROUP, PLLC; Robert L. Scott, Esq.

(57)               ABSTRACT

A conversion device includes: a unit attribute update unit that specifies a unit associated with a representative value approximating a feature vector for a biological signal, and updates a representative value and energy of the specified unit; a unit update unit that, when a plurality of feature vectors outside a predetermined range of a representative value of a unit of the unit data are acquired within a predetermined time, adds data for a new unit identifier to unit data; a class update unit that, when there is no class including a unit having energy within a predetermined range of energy of the new unit, adds data for a new class identifier to class data; and a motion update unit that updates motion data by associating, with an identifier of a class acquired after updating the class data, an identifier of a motion corresponding to the class.

5 Claims, 14 Drawing Sheets

(51) Int. Cl.
    *G06F 3/01*         (2006.01)
    *A61F 2/70*         (2006.01)

(56)            References Cited

FOREIGN PATENT DOCUMENTS

| JP | 4517537 | B2 | 8/2010 |
| JP | 4687935 | B2 | 5/2011 |

12 UNIT DATA

| UNIT IDENTIFIER | REPRESENTATIVE VALUE | ENERGY |
|---|---|---|
| ... | ... | ... |
| ... | ... | ... |

FIG. 7

13 CLASS DATA

| CLASS IDENTIFIER | UNIT IDENTIFIER INCLUDED IN CLASS |
|---|---|
| ... | ... |
| ... | ... |

FIG. 8

14 MOTION DATA

| CLASS IDENTIFIER | MOTION IDENTIFIER CORRESPONDING TO CLASS |
|---|---|
| ... | ... |
| ... | ... |

FIG. 13

13a CLASS DATA

| CLASS IDENTIFIER | RANGE OF FEATURE VECTOR | ENERGY |
|---|---|---|
| ... | ... | ... |
| ... | ... | ... |

FIG. 14

| DATA SET | THE NUMBER OF EVALUATION UNITS | THE NUMBER OF LEARNED UNITS | THE NUMBER OF DELETED UNITS | THE NUMBER OF EXTRACTED UNITS |
|---|---|---|---|---|
| 1 | 5415 | 5413 | 5116(94.51%) | 297(5.45%) |
| 2 | 5413 | 5411 | 5200(96.10%) | 211(3.90%) |
| 3 | 5414 | 5416 | 5213(96.25%) | 203(3.75%) |
| AVERAGE | – | – | 95.62% | 4.38% |

FIG. 15

| DATA SET | VERIFICATION SUBJECT | COMPARISON SUBJECT |
|---|---|---|
| 1 | 84.37 | 80.49 |
| 2 | 83.21 | 82.40 |
| 3 | 80.99 | 77.96 |
| AVERAGE | 82.86 | 80.28 |

| | rst | opn | pwg | prg | ltg | flx | ext | prn | spn |
|---|---|---|---|---|---|---|---|---|---|
| rst | 100 | 0 | 0 | 0 | 0 | 0 | 0 | 0 | 0 |
| opn | 0 | 81 | 0 | 0 | 0 | 0 | 0 | 17 | 0 |
| pwg | 0 | 0 | 100 | 0 | 0 | 0 | 0 | 0 | 0 |
| prg | 0 | 7 | 0 | 83 | 10 | 0 | 0 | 0 | 0 |
| ltg | 0 | 0 | 5 | 0 | 95 | 0 | 0 | 0 | 0 |
| flx | 0 | 0 | 0 | 0 | 0 | 100 | 0 | 0 | 0 |
| ext | 0 | 0 | 0 | 0 | 0 | 0 | 100 | 0 | 0 |
| prn | 0 | 0 | 0 | 0 | 0 | 0 | 0 | 100 | 0 |
| spn | 0 | 53 | 0 | 0 | 0 | 0 | 0 | 47 | 0 |

(b)

| | rst | opn | pwg | prg | ltg | flx | ext | prn | spn |
|---|---|---|---|---|---|---|---|---|---|
| rst | 100 | 0 | 0 | 0 | 0 | 0 | 0 | 0 | 0 |
| opn | 0 | 86 | 0 | 0 | 0 | 0 | 0 | 14 | 0 |
| pwg | 0 | 0 | 88 | 1 | 11 | 0 | 0 | 0 | 0 |
| prg | 0 | 22 | 0 | 76 | 2 | 0 | 0 | 0 | 0 |
| ltg | 0 | 0 | 0 | 0 | 100 | 0 | 0 | 0 | 0 |
| flx | 0 | 0 | 0 | 0 | 0 | 100 | 0 | 0 | 0 |
| ext | 0 | 0 | 0 | 0 | 0 | 0 | 100 | 0 | 0 |
| prn | 0 | 0 | 0 | 0 | 0 | 0 | 0 | 100 | 0 |
| spn | 0 | 83 | 0 | 0 | 2 | 0 | 0 | 15 | 0 |

(c)

| | rst | opn | pwg | prg | ltg | flx | ext | prn | spn |
|---|---|---|---|---|---|---|---|---|---|
| rst | 100 | 0 | 0 | 0 | 0 | 0 | 0 | 0 | 0 |
| opn | 0 | 94 | 0 | 0 | 0 | 0 | 0 | 6 | 0 |
| pwg | 0 | 0 | 100 | 0 | 0 | 0 | 0 | 0 | 0 |
| prg | 0 | 8 | 12 | 60 | 15 | 0 | 0 | 5 | 0 |
| ltg | 0 | 0 | 9 | 0 | 91 | 0 | 0 | 0 | 0 |
| flx | 0 | 0 | 0 | 0 | 0 | 100 | 0 | 0 | 0 |
| ext | 0 | 16 | 0 | 0 | 0 | 0 | 84 | 0 | 0 |
| prn | 0 | 0 | 0 | 0 | 0 | 0 | 0 | 100 | 0 |
| spn | 0 | 66 | 0 | 0 | 0 | 0 | 0 | 34 | 0 |

(d)

| | rst | opn | pwg | prg | ltg | flx | ext | prn | spn |
|---|---|---|---|---|---|---|---|---|---|
| rst | 100 | 0 | 0 | 0 | 0 | 0 | 0 | 0 | 0 |
| opn | 0 | 77 | 0 | 0 | 0 | 0 | 0 | 23 | 0 |
| pwg | 0 | 0 | 100 | 0 | 0 | 0 | 0 | 0 | 0 |
| prg | 0 | 7 | 11 | 59 | 18 | 0 | 0 | 5 | 0 |
| ltg | 0 | 0 | 0 | 0 | 98 | 0 | 0 | 2 | 0 |
| flx | 0 | 0 | 0 | 0 | 0 | 100 | 0 | 0 | 0 |
| ext | 0 | 0 | 0 | 0 | 0 | 0 | 91 | 9 | 0 |
| prn | 0 | 0 | 0 | 0 | 0 | 0 | 0 | 100 | 0 |
| spn | 0 | 50 | 0 | 0 | 0 | 0 | 0 | 50 | 0 |

(e)

| | rst | opn | pwg | prg | ltg | flx | ext | prn | spn |
|---|---|---|---|---|---|---|---|---|---|
| rst | 100 | 0 | 0 | 0 | 0 | 0 | 0 | 0 | 0 |
| opn | 0 | 84 | 0 | 0 | 0 | 0 | 0 | 16 | 0 |
| pwg | 0 | 0 | 96 | 0 | 4 | 0 | 0 | 0 | 0 |
| prg | 0 | 28 | 0 | 61 | 11 | 0 | 0 | 0 | 0 |
| ltg | 0 | 0 | 0 | 0 | 100 | 0 | 0 | 0 | 0 |
| flx | 0 | 0 | 0 | 0 | 0 | 100 | 0 | 0 | 0 |
| ext | 0 | 0 | 0 | 0 | 0 | 0 | 100 | 0 | 0 |
| prn | 0 | 0 | 0 | 0 | 0 | 0 | 0 | 100 | 0 |
| spn | 0 | 77 | 0 | 0 | 1 | 0 | 0 | 22 | 0 |

(f)

| | rst | opn | pwg | prg | ltg | flx | ext | prn | spn |
|---|---|---|---|---|---|---|---|---|---|
| rst | 100 | 0 | 0 | 0 | 0 | 0 | 0 | 0 | 0 |
| opn | 0 | 85 | 0 | 0 | 0 | 0 | 0 | 15 | 0 |
| pwg | 0 | 0 | 100 | 0 | 0 | 0 | 0 | 0 | 0 |
| prg | 0 | 8 | 30 | 34 | 23 | 0 | 0 | 4 | 1 |
| ltg | 0 | 0 | 0 | 0 | 100 | 0 | 0 | 0 | 0 |
| flx | 0 | 0 | 0 | 0 | 0 | 100 | 0 | 0 | 0 |
| ext | 0 | 0 | 0 | 0 | 0 | 0 | 83 | 17 | 0 |
| prn | 0 | 0 | 0 | 0 | 0 | 0 | 0 | 100 | 0 |
| spn | 0 | 40 | 0 | 0 | 0 | 0 | 0 | 60 | 0 | rst: REST
opn: OPEN PALM
pwg: POWER GRASP
prg: PRECISION GRASP
ltg: LATERAL GRASP
flx: WRIST FLEXION
ext: WRIST EXTENSION
prn: WRIST PRONATION
spn: WRIST SUPINATION FIG. 18
(a)
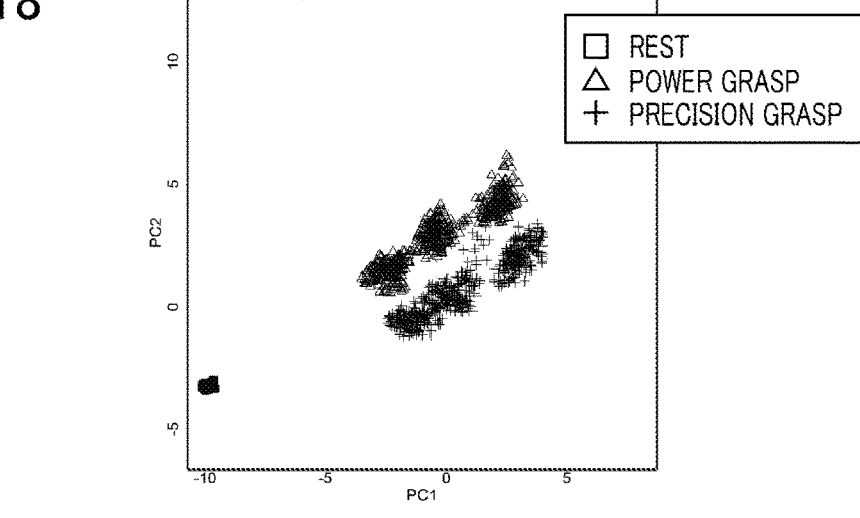
(b)
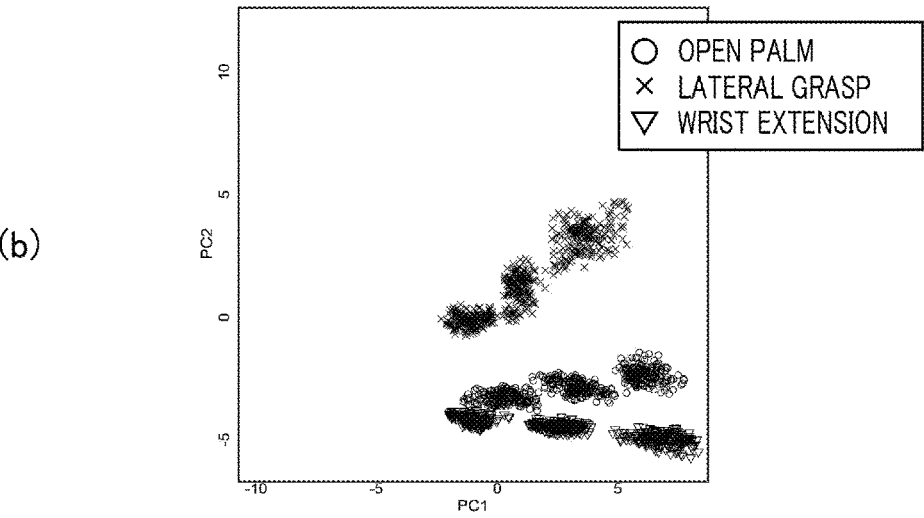
(c)
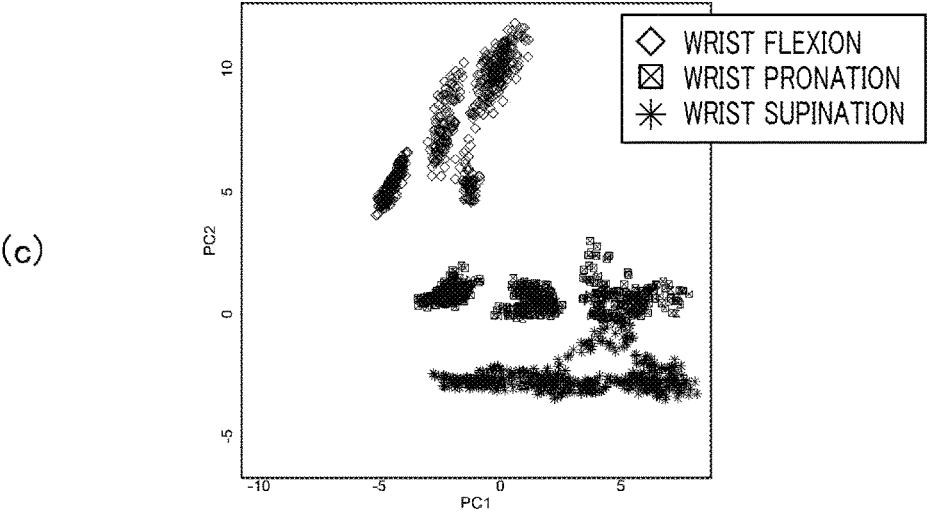

1

RECORDING MEDIUM STORING CONVERSION PROGRAM AND CONVERSION DEVICE

CROSS-REFERENCE TO RELATED APPLICATIONS

This application is based upon and claims the benefit of priority from PCT International Application No. PCT/JP2021/000577, filed Jan. 8, 2021, and Japanese Patent Application No. 2020-002645, filed Jan. 10, 2020; the entire contents of all of which are incorporated herein by reference.

TECHNICAL FIELD

The present invention relates to a recording medium storing a conversion program and a conversion device for converting a biological signal generated in association with a human activity into an instruction signal for activating a robot.

BACKGROUND ART

There are myoelectric hands which output motion signals for electric hands with a myoelectric potential of a user as input. In order to associate a myoelectric potential with a motion signal, there are systems in which a user inputs a teaching signal for the myoelectric potential (Patent Literature 1 and Patent Literature 2). The teaching signal is the users intended motion of the electric hand for the myoelectric potential. In this system, the association between the myoelectric potential and the motion of the electric hand is learned by using data, which is acquired by associating a feature vector of the myoelectric potential with the teaching signal, as teacher data.

CITATION LIST

Patent Literature

Patent Literature 1: JP Patent No. 4517537
Patent Literature 2: JP Patent No. 4687935

SUMMARY OF THE INVENTION

Technical Problem

In the method disclosed in Patent Literature 1 and Patent Literature 2, the user may need to take the trouble of inputting the motion of an electric hand intended by the user with respect to a myoelectric potential. In addition, the user may change the association between a myoelectric potential and a motion of an electric hand, and thus effective learning may be difficult.

As described above, in the present situation, it is difficult to learn the association between a biological signal such as a myoelectric potential and a motion of a robot such as an electric hand without using teacher data.

Accordingly, an object of the present invention is to provide a technique capable of learning the association between a biological signal and a motion of a robot without using teacher data.

Solution to Problem

In order to solve the above problem, a first feature of the present invention relates to a conversion program for converting a biological signal generated in association with a human activity into an instruction signal for activating a robot. The conversion program according to the first feature of the present invention causes a computer to function as: an acquisition unit configured to sequentially acquire feature vectors for a biological signal; a unit data storage unit configured to store unit data which associates an identifier of a unit, a representative value corresponding to a feature vector belonging to the unit, and energy corresponding to the feature vector belonging to the unit; a class data storage unit configured to store class data that associates an identifier of a class with identifier of a unit included in the class; a unit attribute update unit configured to attenuate energy of the unit as time elapses, and specify a unit associated with a representative value approximating a new feature vector acquired by the acquisition unit, and update a representative value and energy of the specified unit based on the new feature vector; a unit update unit configured to delete from the unit data, data related to an identifier of a unit satisfying a predetermined condition due to attenuation of the energy, and when the acquisition unit acquires a plurality of similar feature vectors outside a predetermined range of a representative value of the unit of the unit data within a predetermined time, add to the unit data, data associating an identifier of a new unit with a representative value and energy of the new unit; a class update unit configured to, when there is another unit having an attribute within a predetermined range of an attribute of the new unit, add an identifier of the new unit in the class data as an identifier of a unit included in a class having the identifier of the other unit associated therewith, when there is no unit having an attribute within a predetermined range of an attribute of the new unit, add data associating an identifier of a new class with an identifier of the new unit to the class data, and when the unit data has no data related to an identifier of a unit associated with the class identifier the class data, delete the class identifier from the class data; a motion update unit configured to update motion data associating, with an identifier of a class acquired after updating the class data, an identifier of a motion corresponding to the class; and an instruction output unit configured to, when the acquisition unit acquires a feature vector, specify an identifier of a class including a unit to which the acquired feature vector belongs, and output an instruction signal corresponding to the specified identifier of the class by referring to the motion data.

The energy may be expressed in terms of position and energy intensity in a feature field with parameters of the feature vector as axes, and the unit attribute update unit may set energy at a position corresponding to the feature vector in the feature field when the acquisition unit acquires the new feature vector, and may update the energy such that the set energy diffuses and attenuates as time elapses after the new feature vector is acquired.

The motion update unit may randomly change an identifier of a motion corresponding to the class.

In a case where the motion update unit attempts to change an association between an identifier of a motion and a class, the motion update unit may change an identifier of a motion of a class to be changed when the motion identifier of the class to be changed is the same as an identifier of a motion of another class and energy of the class to be changed is greater than energy of the other class, and the motion update unit may not change the motion identifier of the class to be changed when energy of the class to be changed is smaller than energy of the other class.

A second feature of the present invention relates to a conversion program for converting a biological signal generated in association with a human activity into an instruction signal for activating a robot. The conversion program according to the second feature of the present invention causes a computer to function as: an acquisition unit configured to sequentially acquire feature vectors for a biological signal; a class data storage unit configured to store class data that associates an identifier of a class, a range of a feature vector included in the class, and energy of the class; a class update unit configured to attenuate energy of the class as time elapses, delete from the class data, data related to an identifier of a class satisfying a predetermined condition due to attenuation of the energy, increase energy of an identifier of a class corresponding to a new feature vector acquired by the acquisition unit, and when the acquisition unit acquires a plurality of similar feature vectors outside a range of the feature vector of the class data within a predetermined time, add to the class data, data associating an identifier of a new class with a range of a feature vector of the new class and energy of the new class; a motion update unit configured to update motion data by associating with, an identifier of class acquired after updating the class data, an identifier of a motion corresponding to the class; and an instruction output unit configured to, when the acquisition unit acquires a feature vector, specify an identifier of a class to which the acquired feature vector belongs, and output an instruction signal corresponding to the specified identifier of the class by referring to the motion data.

A third feature of the present invention relates to a conversion device including: a storage device configured to store a conversion program according to the first or second feature of the present invention; and a processing device configured to execute the conversion program stored in the storage device.

Advantageous Effects of the Invention

The present invention makes it possible to provide a technique capable of learning the association between a biological signal and a motion of a robot without using teacher data.

BRIEF DESCRIPTION OF THE DRAWINGS

FIG. 2 illustrates classes used in a conversion device according to the embodiment of the present invention.

FIG. 6 is a diagram illustrating an example of a data structure for unit data.

FIG. 7 is a diagram illustrating an example of a data structure for class data.

FIG. 8 is a diagram illustrating an example of a data structure for motion data.

FIG. 13 is a diagram illustrating an example of a data structure for class data according to the first modification.

FIG. 14 illustrates the result of comparing units of evaluation data and units of learning data in a second modification.

FIG. 15 illustrates the result of comparing the identification rates of verification subjects and comparison subjects in the second modification.

FIGS. 16(a), (b), (c), (d), (e) and (f) are diagrams illustrating the identification rates of respective motions of the verification subjects and the comparison subjects.

FIGS. 18(a), 18(b) and 18(c) illustrate myoelectric features when the myoelectric hand H is activated by three target gripping forces with nine motions.

DESCRIPTION OF EMBODIMENTS

Next, an embodiment of the present invention will be described with reference to the drawings. In the following drawings, the same or similar parts are denoted by the same or similar numerals.

(Robot Operation System)

A conversion device 1 according to an embodiment of the present invention converts a biological signal generated in accordance with the activity of a user R into an instruction signal for activating a robot. The conversion device 1 is used, for example, in a robot operation system 5 illustrated in FIG. 1. In the embodiment of the present invention, the biological signal is a myoelectric potential, and the robot is a myoelectric hand H.

Figure 1:
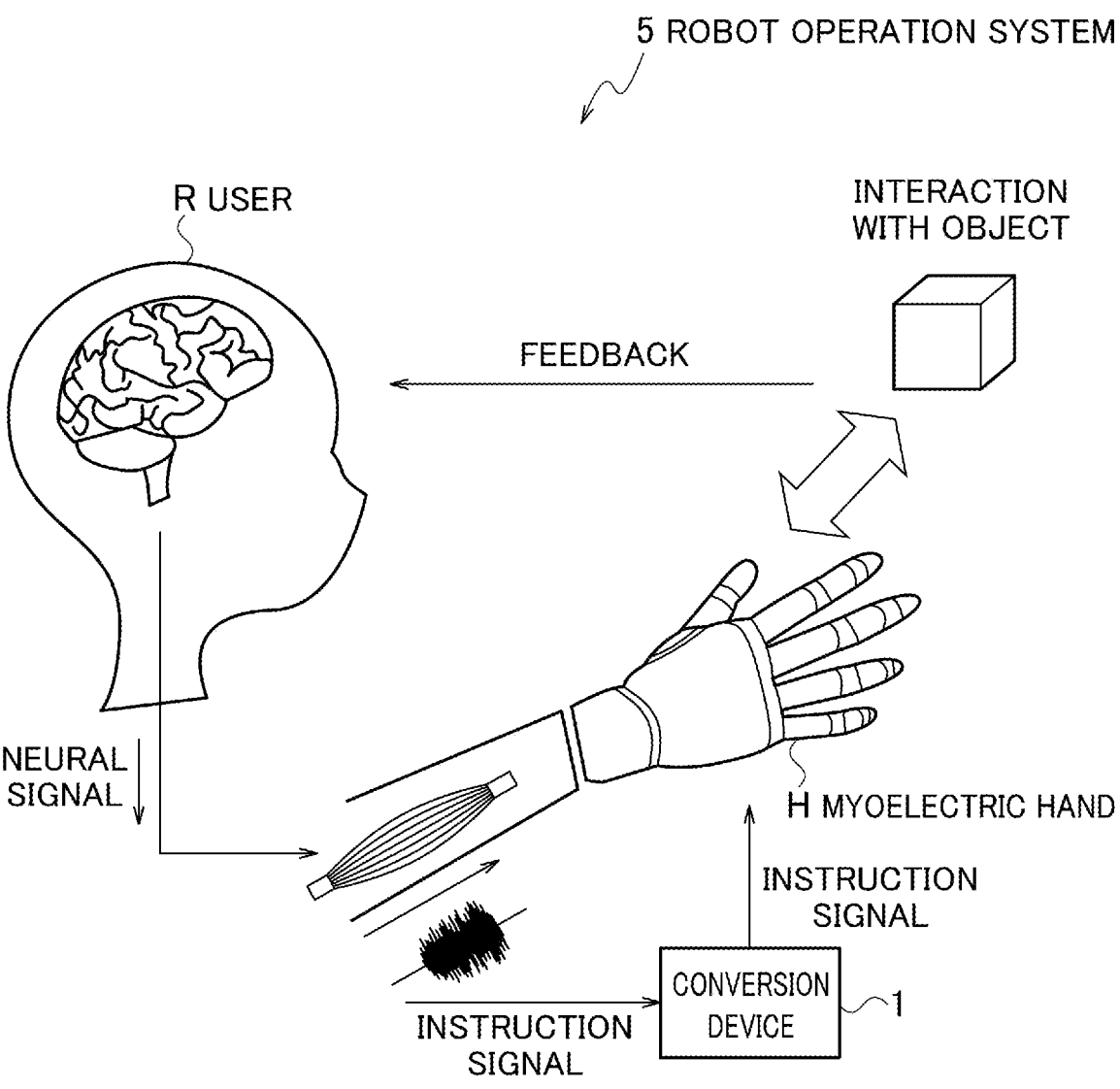
FIG. 1 is a schematic diagram of a robot operation system according to an embodiment of the present invention.

As illustrated in FIG. 1, an intention of the user R is transmitted as a neural signal to desired muscle cells of the user R, and the desired muscle cells contract. The contraction of the muscle cells is detected by means of a myoelectric potential. The conversion device 1 detects a transition of the myoelectric potential in the muscle, converts the change of the myoelectric potential into a motion signal for the robot, and thereby activates the myoelectric hand H.

At this time, the conversion device 1 learns the association between the change of the myoelectric potential and the motion signal for the myoelectric hand H. Since the conversion device 1 learns without teacher data, the load on the user R is small.

In order to achieve a desired motion of the myoelectric hand H, there are several ways of moving the muscle cells of the user R, and the way in which the myoelectric hand H of the user R is used may also change as time elapses. When the association between the myoelectric potential detected in accordance with the muscle contraction and the motion for grasping an object is correctly performed, the user R can perform the motion for grasping an object. In this process, a person learns by changing how muscle cells contract to grasp an object. It is necessary for the conversion device 1 to appropriately assign a motion of the myoelectric hand H to the contraction method of the muscle cells which changes in accordance with learning the association between the myoelectric potential and the motion by the user R.

Even in such a case, since the conversion device 1 according to the embodiment of the present invention learns by detecting a change in the motion of the muscle cells of the user R and allocating a motion of the myoelectric hand H, the operability of the myoelectric hand H for the user R can be improved.

In the embodiment of the present invention, an example of the robot will be described as the myoelectric hand H, but the present invention is not limited thereto. For example, the present invention can be employed for various kinds of robots such as an industrial robot, a nursing robot, and an agricultural robot which perform a predetermined motion, in addition to a robot which compensates for a defective part of a human such as a prosthetic arm and a prosthetic leg.

In the embodiment of the present invention, a description will be given regarding the case in which the conversion device 1 is positioned in the space where the user R and the robot are present, but the present invention is not limited to this case. For example, like the case where the user R operates a robot at a remote place, the conversion device 1 may be arranged in a space different from that of the user R or the robot, or in a space different from that of the user R and the robot. Further, although a description will be given regarding the case where the conversion device 1 converts a biological signal into an instruction signal for a robot in order for one user R to operate one robot, a biological signal may be converted into an instruction signal for a robot for each pair of a user R and a robot.

(Logic of Conversion Device)

The logic of the conversion device 1 according to the embodiment of the present invention will be described with reference to FIGS. 2 to 4.

When the user R changes the contraction method of the muscles when operating the myoelectric hand H, the detected myoelectric potential changes. Accordingly, in the learning in the embodiment of the present invention, since the teacher data constantly changes and the optimization target is unknown, it is necessary to optimize parameters by the concept of adaptation. A parameter corresponds to instruction signal input to the myoelectric hand H in the embodiment of the present invention.

In adaptation, optimization is performed depending on whether the environment allows the parameters to persist. In a case of a robot is the myoelectric hand H as in the embodiment of the present invention, the environment as the actual user R. It is necessary to acquire information on whether adaptation is possible depending on whether or not the user R uses a motion of the myoelectric hand H associated with a myoelectric potential. The association between myoelectric potentials and motions of the myoelectric hand H constantly changes.

The environment (user R) using a motion of the myoelectric hand H associated with a myoelectric potential means that a signal based on a myoelectric potential is input to the myoelectric hand H. Further, the environment using a motion of the robot associated with a myoelectric potential determines that the motion of the robot associated with the myoelectric potential is appropriate.

In the conversion device 1 according to the embodiment of the present invention, a unit corresponding to a myoelectric potential is defined. The unit persists when the myoelectric potential corresponding to the unit is input, and is eliminated when the myoelectric potential corresponding to the unit is not input.

The unit is associated with a class, and the class is associated with a motion of the robot. The identifiers of one or more units belonging to a class ω are associated with the class ω. When the optimization direction of the association between the class and motion of the robot matches the desired direction of the environment, the unit belonging to the class is enhanced. When the optimization direction does not match the desired direction of the environment, the unit is eliminated, and the association of the motion of the robot associated with the unit is also eliminated.

In the embodiment of the present invention, a myoelectric potential is treated as a feature vector v specified from a myoelectric potential acquired during a predetermined time. The feature vector v is a vector converted from a time series signal by Fast Fourier Transformation (FFT) or the like. Myoelectric potential may be detected from one location or from a plurality of locations.

In the embodiment of the present invention, the feature vector v is associated with the unit u, and the unit u is associated with the class ω. The number of classes ω correspond to the types of instruction signals input to the robot. The class ω may be associated with a plurality of units u.

A representative value and energy are associated with the unit u. The representative value is a representative value of the feature vector v belonging to the unit u, which is, for example, an average value or a median value.

Each unit $u_i$ is expressed by a representative value $V_{tpy}$ as illustrated in Equation (1).

[Math. 1]

$$u_i = V_{tpy}(V(t)), (I=1,2, \ldots, M) \qquad \text{Equation (1)}$$

$$\text{e.g. } V_{tpy}(V(t)) = \text{Average}(V(t))$$

The energy of the unit u is increased by the input of a feature vector v similar to the unit u, and attenuates as time elapses. In the embodiment of the present invention, the energy has the property of radially propagating from the center position of the feature vector v belonging to the unit u, in, the coordinate space (feature field) corresponding to the parameter of the feature vector v.

When a new feature vector v is acquired, it is integrated into a unit u having a representative value similar to the feature vector v. For the unit u integrated with the new feature vector v, the representative value is updated and the energy is further amplified. The unit u does not need to retain the new feature vector v, and it is sufficient for the representative value and energy to be updated by using the new feature vector v.

When there is no unit u having a representative value similar to the acquired new feature vector v and when a plurality of feature vectors similar to each other are acquired within a predetermined time, a new unit u is generated. The new unit u is integrated into a nearby class ω. When there is no nearby class ω, a new class ω is generated.

Here, the number of classes ω is equal to or less than the number of types of instruction signals input to the myoelectric hand H. Accordingly, in a case where a new class ω is generated, when the number of existing classes ω is equal to the number of types of instruction signals input to the myoelectric hand H, the class ω having the lowest evaluation value among the existing classes ω is deleted. This evaluation value is a value acquired by integrating the energy of each unit u belonging to the class ω. The evaluation value is, for example, the total energy of each coordinate of each unit u, the sum of energies of the peaks of respective units u, and the time since the last input of a feature vector, which is an index indicating that the feature vectors belonging to the unit are continuously input.

Further, the energy of a unit u into which new feature vectors v are not integrated continues to attenuate, and such a unit u is eventually eliminated. Further, when the units u associated with a class are eliminated, the class ω is also eliminated.

In this way, the units u repeat generation and elimination according to the input state of the feature vectors v. Further, as the units u are generated and eliminated, the classes ω are also repeatedly generated and eliminated.

A class ω will be described with reference to FIG. 2. In FIG. 2, the class $\omega_k$ (k=1, 2, 3, 4, 5) is defined.

The class ω integrates units u having similar energy in the feature field Ω. The feature field illustrated in FIG. 2 is defined by axes corresponding to the parameters of the feature vectors v. In the example illustrated in FIG. 2, the feature field is defined by two axes; however, the number of axes are not limited to two axes.

The feature field Ω is expressed as a set of classes ω and is defined as Equation (2).

[Math. 2]

$$\Omega=\{\omega_k\},(k=1,2,\ldots,N) \qquad \text{Equation (2)}$$

Here, the class ω is a field that functions as a spatial spreading and propagating medium. The class ω has dynamics described by a diffusion equation or a wave equation of Equation (3-1), Equation (3-2) or Equation (3-3). Thus, the input generated at any point on the class ω has a diffusion property according to the dynamics.

[Math. 3]

$$\frac{\partial \omega_k}{\partial t} = D\nabla^2 \omega_k = D\left(\frac{\partial^2 \omega_k}{\partial x_1^2} + \frac{\partial^2 \omega_k}{\partial x_2^2} + \ldots + \frac{\partial^2 \omega_k}{\partial x_{N_{dim}}^2}\right) \qquad \text{Equation (3-1)}$$

$$\frac{1}{dt}\left({}^k U_{x_1,x_2,\ldots,x_{N_{dim}}}^{t+1} - {}^k U_{x_1,x_2,\ldots,x_{N_{dim}}}^{t}\right) =$$

$$\frac{D}{dx_1^2}\left({}^k U_{x_1-1,x_2,\ldots,x_{N_{dim}}}^{t} - \right.$$

$$2^k U_{x_1,x_2,\ldots,x_{N_{dim}}}^{t} + {}^k U_{x_1+1,x_2,\ldots,x_{N_{dim}}}^{t}\right) +$$

$$\frac{D}{dx_2^2}\left({}^k U_{x_1,x_2-1,\ldots,x_{N_{dim}}}^{t} - 2^k U_{x_1,x_2,\ldots,x_{N_{dim}}}^{t} + \right.$$

$${}^k U_{x_1,x_2+1,\ldots,x_{N_{dim}}}^{t}\right) + \ldots + \frac{D}{dx_{N_{dim}}^2}\left({}^k U_{x_1,x_2,\ldots,x_{N_{dim}}-1}^{t} - \right.$$

$$2^k U_{x_1,x_2,\ldots,x_{N_{dim}}}^{t} + {}^k U_{x_1,x_2,\ldots,x_{N_{dim}}+1}^{t}\right) \qquad \text{Equation (3-2)}$$

$${}^k U_{x_1,x_2,\ldots,x_{N_{dim}}}^{t+1} = {}^k U_{x_1,x_2,\ldots,x_{N_{dim}}}^{t} + \Delta^k U_{x_1,x_2,\ldots,x_{N_{dim}}} \qquad \text{Equation (3-3)}$$

$$\left(\Delta^k U_{x_1,x_2,\ldots,x_{N_{dim}}} = \right.$$

$$\frac{Ddt}{dx_1^2}\left({}^k U_{x_1-1,x_2,\ldots,x_{N_{dim}}}^{t} - 2^k U_{x_1,x_2,\ldots,x_{N_{dim}}}^{t} + {}^k U_{x_1+1,x_2,\ldots,x_{N_{dim}}}^{t}\right) +$$

$$\frac{Ddt}{dx_2^2}\left({}^k U_{x_1-1,x_2,\ldots,x_{N_{dim}}}^{t} - 2^k U_{x_1,x_2,\ldots,x_{N_{dim}}}^{t} + {}^k U_{x_1,x_2+1,\ldots,x_{N_{dim}}}^{t}\right) + \ldots +$$

$$\left. \frac{Ddt}{dx_{N_{dim}}^2}\left({}^k U_{x_1,x_2,\ldots,x_{N_{dim}}-1}^{t} - 2^k U_{x_1,x_2,\ldots,x_{N_{dim}}}^{t} + {}^k U_{x_1,x_2,\ldots,x_{N_{dim}}+1}^{t}\right)\right)$$

$N_{dim}$: The number of dimensions (the number of axes in space)

$x_n$: Value of the $n^{th}$ axis (in the present invention, the strength of the myoelectric potential in a certain frequency band)

$${}^k U_{x_1,x_2,\ldots,x_{N_{dim}}}^{t}:$$

Magnitude of energy of time$^t$, class$^k$ at a vector ( $x_1$, $x_2$, . . . , $x_{N_{dim}}$ ) (one point in space)

$$\Delta^k U_{x_1,x_2,\ldots,x_{N_{dim}}}:$$

Amount of change per unit time (when the time changes from t to t+1

Figure 3:
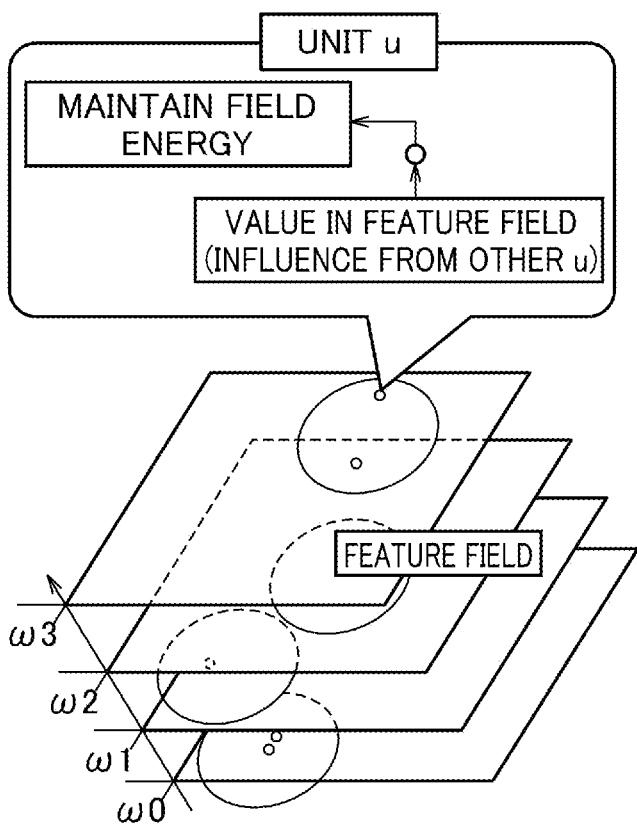
FIG. 3 is a diagram illustrating the relationship between classes and units used in the conversion device according to the embodiment of the present invention.

As illustrated in FIG. 3, each class ω includes a plurality of units u. When a new feature vector v is input, energy of a unit u having a representative value similar to the new feature vector v is amplified. Further, the energy of the class ω including the unit u whose energy has been amplified is amplified, and the class ω is maintained. Meanwhile, when a feature vector v is not input, the energy of each unit u continues to attenuate as time elapses, and thus units u are eliminated, and classes ω are also eliminated.

Each class ω is associated with a motion label A of the robot in a label space. A motion label corresponds to a motion signal input to the robot. Each class ω and a motion label A are initially associated with each other at random. When the robot is activated as intended by the user, the user R continues to use this association. Specifically, since the user R continues to input feature vectors v corresponding to the class, the energy of the class increases and the association continues. However, when the robot does not operate as intended by the user, the user R does not use this association. Specifically, since the user R does not input feature vectors v corresponding to the class, the energy corresponding to the class ω decreases, and the units are eventually eliminated.

In the embodiment of the present invention, the association between a certain class ω and a motion label A of the robot appropriately changes in order to find a more optimal association. For a certain motion label A, when the changed class ω collides with an existing class ω, the class ω having the larger energy is associated with the motion label A. The smaller energy class ω of the two collided classes is associated with a motion label A other than the currently associated motion label A. In other words, the energy of the class ω is an inertial force to remain in that place, and a repulsive force when competing with other classes. The energy of the class ω is acquired integrating the energy of the units belonging to the class ω. The energy of the class ω is, for example, the total energy of each coordinate of each unit u, the sum of energies of the peaks of the respective units u, or the like.

Figure 4:
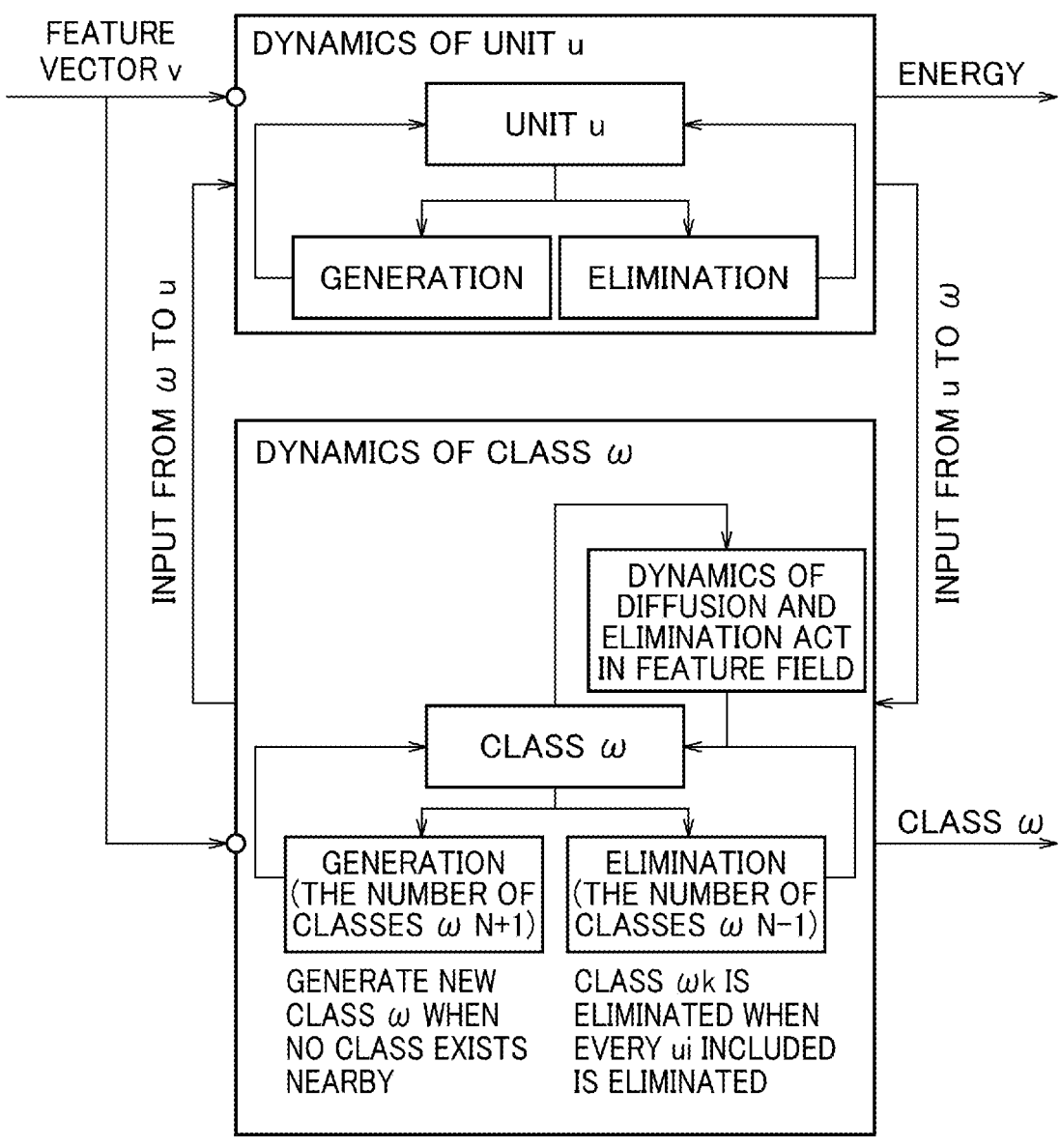
FIG. 4 illustrates generation and elimination of the class and generation and elimination of the unit used in the conversion device according to the embodiment of the present invention.

With reference to FIG. 4, the unit and the class ω will be described. Both the unit u and the class ω repeat generation and elimination in accordance with the usage situation of the user R.

A unit u is generated when a feature vector not similar to a representative value of an existing unit u is input more than a predetermined number of times within a predetermined time. When a unit u is generated, a representative value and energy are set based on a plurality of input feature vectors. When a feature vector similar to a representative value of an existing unit u is input, the feature vector is integrated into the unit u having the similar representative value, and the representative value and energy of the unit u are updated.

Since the energy of a unit u attenuates as time elapses, when the energy becomes a predetermined value or less, the unit in is eliminated. A unit u acts on a class ω and exerts a force at the position of the class ω. This is called an input from a unit u to a class ω.

When a unit u is generated and a class ω similar to the unit u does not exist, a new class ω is generated. The number of classes ω is controlled to be equal to or less than the number of motion labels A. When a new class ω is generated and the number of the existing classes ω reaches the number of the motion labels A, the class ω having the lowest evaluation value among the existing classes ω is eliminated.

A class ω is a field that functions as a spatial spreading and propagating medium. A class ω has dynamics described by a diffusion equation or a wave equation of Equation (3). Thus, the input of a vector v, which is generated at any point on a class ω, to a unit u has a diffusion property according to the dynamics. The value of the energy of a class ω is observable from a unit u. This is called an input from a class ω to a unit u.

A class ω also includes a plurality of units u. The plurality of units u included in one class ω interact within the class ω. (Conversion Device)

Figure 5:
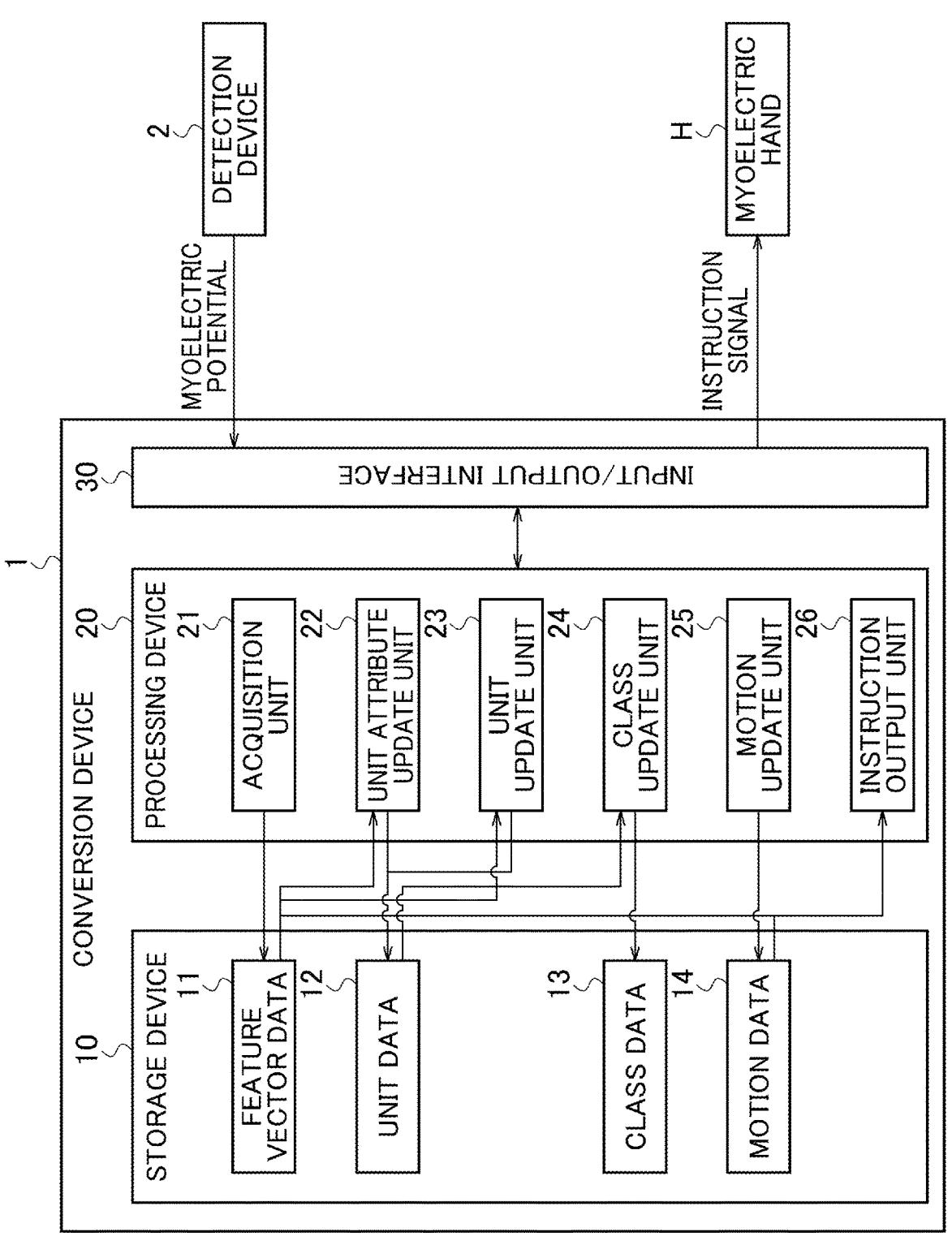
FIG. 5 is a diagram for explaining a hardware configuration and functional blocks of the conversion device according to the embodiment of the present invention.

With reference to FIG. 5, a conversion device 1 according to the embodiment of the present invention will be described. The conversion device 1 converts a myoelectric potential generated in accordance with a human activity into an instruction signal for activating the myoelectric hand H.

The conversion device 1 is a general computer including a storage device 10, a processing device 20, and an input/output interface 30. A general computer executes a conversion program to realize the functions illustrated in FIG. 5. The conversion program can be stored in a computer-readable recording medium such as an HDD, an SSD, a universal serial bus (USB) memory, a CD (compact disc), a DVD (digital versatile disc), or can be distributed over a network.

The storage device 10 is a ROM (read only memory), a RAM (random access memory), a hard disk, an SSD (solid state drive), etc., and stores various data such as input data, output data, and intermediate data for the processing device 20 to perform processing. The processing device 20 is a CPU (central processing unit) that reads and writes data stored in the storage device 10, and inputs and outputs data to and from the input/output interface 30, thereby performing processing in the conversion device 1. The input/output interface 30 inputs data input from an input device such as a mouse and a keyboard to the processing device 20, and outputs data output from the processing device 20 to an output device such as a printer and a display device. The input/output interface 30 may be an interface for communicating with other computers.

The conversion device 1 according to the embodiment of the present invention is connected to the detection device 2 and the myoelectric hand H via the input/output interface 30. The detection device 2 acquires a biological signal of the user R and inputs it to the conversion device 1. In the embodiment of the present invention, the detection device 2 sequentially acquires a myoelectric potential from a sensor attached to the skin of the user R and inputs the myoelectric potential to the conversion device 1. When an instruction signal output from the conversion device 1 is input, the myoelectric hand H is activated according to the instruction signal.

The storage device 10 stores a conversion program, stores feature vector data 11, unit data 12, class data 13, and motion data 14. The portions of the storage device 10 for storing the feature vector data 11, the unit data 12, the class data 13, and the motion data 14 are referred to as a feature vector data storage unit, a unit data storage unit, a class data storage unit, and a motion data storage unit, respectively.

The feature vector data 11 stores feature vectors sequentially acquired by an acquisition unit 21 described later.

As illustrated in FIG. 6, the unit data 12 associates an identifier of a unit, a representative value corresponding to a feature vector belonging to the unit, and energy corresponding to the feature vector belonging to the unit.

The representative value is an average value, a median value, or the like of the feature vector belonging to the unit corresponding to the representative value. The representative value is referred to when determining which unit the feature vector belongs to when a new feature vector is input.

The energy is amplified by an input of a feature vector, and attenuates as time elapses. The energy is an indicator of whether the user R uses the unit continuously.

Figure 2:
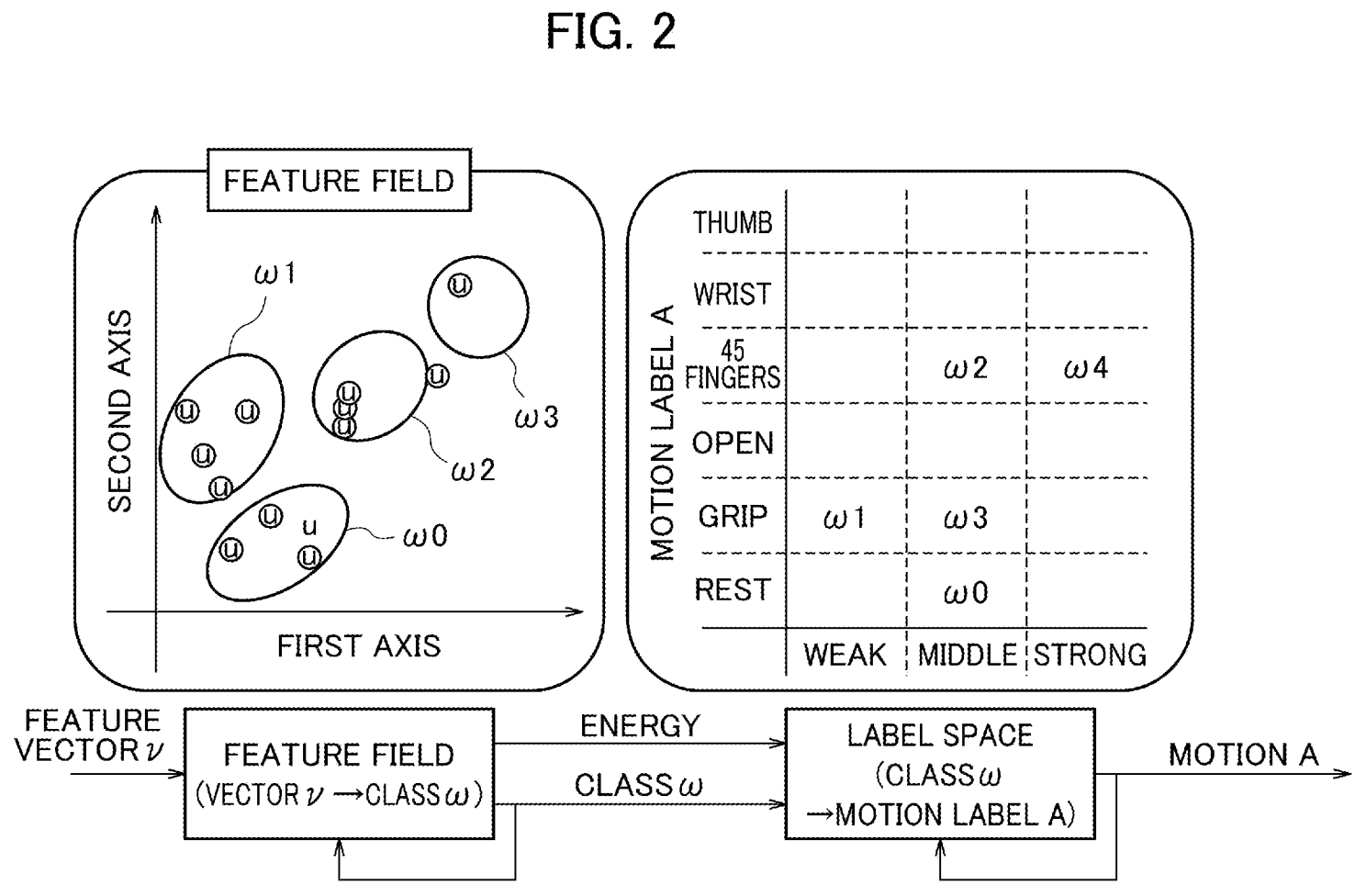

In the embodiment of the present invention, the energy is expressed in terms of position and energy intensity, in the feature Feld with the parameters of the feature vectors as axes, as illustrated in FIG. 2. The energy is transmitted from the position corresponding to a feature vector, which is associated with a unit, to the periphery of the feature vector, and attenuates as time elapses. In other words, the energy is defined by a set of a position in the feature field and a value of the energy at the position. For example, in the feature field, the amount of energy to be amplified for an input feature vector is greater at the position corresponding to the input feature vector, and decreases as the distance from the position increases. In this case, the energy is specified, for example, from the added feature vector and the time when the feature vector is added. Since the energy attenuates as time elapses, the total amount of energy when diffused is less than the energy when the feature vector is input.

The addition of energy is repeated each time a feature vector is input. For example, by repeatedly inputting a similar feature vector, a state in which energy around the feature vector is high is maintained.

In the embodiment of the present invention, a description will be given regarding the case where the energy propagates in the feature field, but the present invention is not limited thereto. For example, the energy may be a value given to one unit, which may increase with the input of a feature vector and attenuate as time elapses.

As illustrated in FIG. 7, the class data 13 associates a class identifier with an identifier of a unit included in the class. The identifiers of a plurality of units may be associated with the identifiers of one class. The upper limit of the number of pieces of class data is the upper limit of the number of motion signals output by the conversion device 1.

As illustrated in FIG. 8, the motion data 14 associates a class identifier with an identifier of a motion of the myoelectric hand H corresponding to the class. The motion data 14 is referred to when a myoelectric potential of the user R is input and converted into a motion signal for the myoelectric hand H.

The processing device 20 includes an acquisition unit 21, a unit attribute update unit 22, a unit update unit 23, a class update unit 24, a motion update unit 25 and an instruction output unit 26.

The acquisition unit 21 sequentially acquires feature vectors of myoelectric potentials (biological signals). The acquisition unit 21 sequentially acquires values of the myoelectric potentials from the detection device 2, and converts the acquired myoelectric potentials into feature vectors.

There are several ways to convert a myoelectric potential into feature vector. The acquisition unit 21 calculates, for example, a histogram of the frequency of a myoelectric potential at each time by means of FFT, and calculates the histogram as a feature vector. The feature vector should represent a feature of the acquired myoelectric potential, regardless of the calculation method. The feature vector is appropriately processed, for example, is generated after noise is removed.

The unit attribute update unit 22 updates an attribute value of a unit. The attribute value of a unit is a representative value and energy.

The unit attribute update unit 22 attenuates the energy of a unit as time elapses. The unit attribute update unit 22 attenuates the energy of a unit at a predetermined timing according to the lapsed time from the timing at which the previous update was carried out. In the embodiment of the present invention, the unit attribute update unit 22 attenuates the energy formed by a certain feature vector, and thus the area influenced by the energy in the feature field also becomes smaller.

When the acquisition unit 21 acquires a new feature vector, the unit attribute update unit 22 specifies a unit associated with a representative value approximating the new feature vector acquired by the acquisition unit 21, and updates the representative value and energy of the specified unit based on the new feature vector.

When the similarity between a new feature vector acquired by the acquisition unit 21 and the representative value of an existing unit is a predetermined value or more, the new feature vector belongs to the existing unit. The unit attribute update unit 22 updates the representative value and energy of the existing unit based on the new feature vector. When there are a plurality of existing units whose similarity between the new feature vector and the representative value is a predetermined value or more, the unit attribute update unit 22 updates an attribute of the unit having the highest similarity.

The unit attribute update unit 22 updates the representative value based on the new feature vector. When the representative value is an average value, the unit attribute update unit 22 updates the average value in consideration of the new feature vector.

When the acquisition unit 21 acquires a new feature vector, the unit attribute update unit 22 sets energy at a position corresponding to the feature vector in the feature field, and updates the energy such that the set energy diffuses and attenuates as time elapses after the new feature vector is acquired. Here, diffusion means that in the coordinate system representing the feature vector, the total amount of energy given to the position corresponding to the feature vector is allocated over a wide range as time elapses. The unit attribute update unit 22 updates the energy such that the total amount of the energy attenuates as time elapses after the new feature vector is acquired. In order for the energy to be eliminated due to attenuation of the energy after the energy diffuses, the rate at which the energy attenuates is controlled to be slower than the rate at which the energy diffuses.

Figure 9:
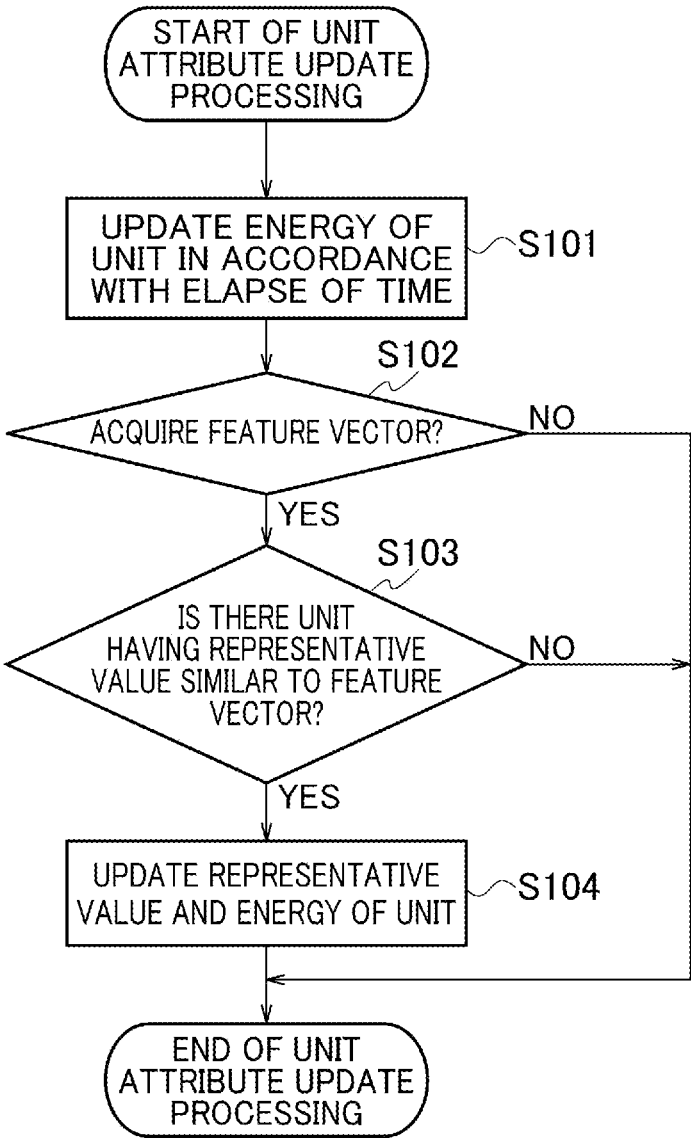
FIG. 9 is a flowchart illustrating the processing of a unit attribute update unit.

With reference to FIG. 9, a description will be given regarding the unit attribute update processing performed by the unit attribute update unit 22. FIG. 9 illustrates processing, which is periodically performed, for updating the energy at a predetermined timing and confirming whether or not there is a feature vector acquired from the previous processing. The processing illustrated in FIG. 9 is merely an example, and the processing is not limited thereto. The unit attribute update unit 22 is not limited to the processing illustrated in FIG. 9. For example, the energy or the like of the unit may be updated at the timing when a feature vector is acquired.

First, in step S101, the unit attribute update unit 22 refers to the unit data 12, and updates the energy of each unit. The energy of each unit diffuses and attenuates.

In step S102, the unit attribute update unit 22 determines whether or not the acquisition unit 21 has acquired a feature vector from the previous processing. When a feature vector is not acquired from the previous processing, the processing ends as it is.

When the acquisition unit 21 has acquired a feature vector from the previous processing, the unit attribute update unit 22 determines in step S103 whether there is a unit having a representative value similar to the feature vector acquired by the acquisition unit 21. When there is no unit the processing ends as it is. When there is a unit, the representative value and energy of the unit in the unit data 12 are updated in step S104.

When there are a plurality of feature vectors acquired by the acquisition unit 21 from the previous processing, the processing of step S104 is repeated for the respective feature vectors.

The unit update unit 23 updates the number of units defined by the unit data 12.

The unit update unit 23 deletes data which is related to an identifier of a unit satisfying a predetermined condition due to the attenuation of energy, from the unit data 12. The unit attribute update unit 22 attenuates the energy of units. When the predetermined condition is satisfied as a result of the attenuation, the unit update unit 23 deletes the data of units satisfying the predetermined condition from the unit data 12. The predetermined condition is, for example, the total amount of energy becomes a predetermined value or less, the range influenced by energy becomes smaller than a predetermined region, or the value of energy at a predetermined position of the feature field becomes a predetermined value or less. That is, with the above predetermined condition, it is determined that the amount of energy has reduced. When the feature vector is not input for a long time and the energy continues to attenuate, the unit update unit 23 determines that the user R does not use the unit, and the unit update unit 23 deletes the unit.

The energy of a unit is amplified when a feature vector corresponding to the unit is input, and attenuates when a feature vector corresponding to the unit is not input. The fact that a feature vector is not input means that the user R does not expect the motion of the myoelectric hand H corresponding to the feature vector and the unit. Units for which no corresponding feature vector is input are deleted.

The unit update unit 23 updates the number of units defined by the unit data 12. In order to output a predetermined instruction signal, the unit update unit 23, based on a situation in which the user R contracts muscle cells by trial and error, increases or decreases the number of units in consideration of changes in the myoelectric potential accompanying the contraction of the muscle cells. The unit update unit 23 can define a class to be used by the user R according to the increase and decrease of the units.

When the acquisition unit 21 acquires a plurality of similar feature vectors outside a predetermined range of the representative values of the units of the unit data 12 within a predetermined time, the unit update unit 23 adds data to the unit data 12 in which an identifier of the new unit is associated with a representative value and energy of the new unit.

When the user R attempts a new motion, the user R repeats the motion many times and expects a desired motion performed by the myoelectric hand H in accordance with the motion. Then, the unit update unit 23 detects this kind of new motion and forms a new unit. In the embodiment of the present invention, when a similar feature vector outside the predetermined range from the representative value of an existing unit is it a predetermined number of times or more, it is determined that the user H is attempting a new motion. Here, the similar feature vectors are such that the similarity between the feature vectors, is a predetermined value or more. A feature vector outside the predetermined range from the representative value of an existing unit is, specifically, a feature vector whose similarity with the representative value of the existing unit is a predetermined value or less.

When an upper limit is set for the number of units and the upper limit is exceeded by an addition of units, the unit update unit 23 may delete the data of the unit having the lowest energy from the unit data 12, and define new unit data in the unit data 12. When the number of similar feature vectors outside the predetermined range of the representative values of the units of the unit data 12 acquired within the predetermined time is less than the predetermined number of times, the unit update unit 23 does not generate a new unit.

Figure 10:
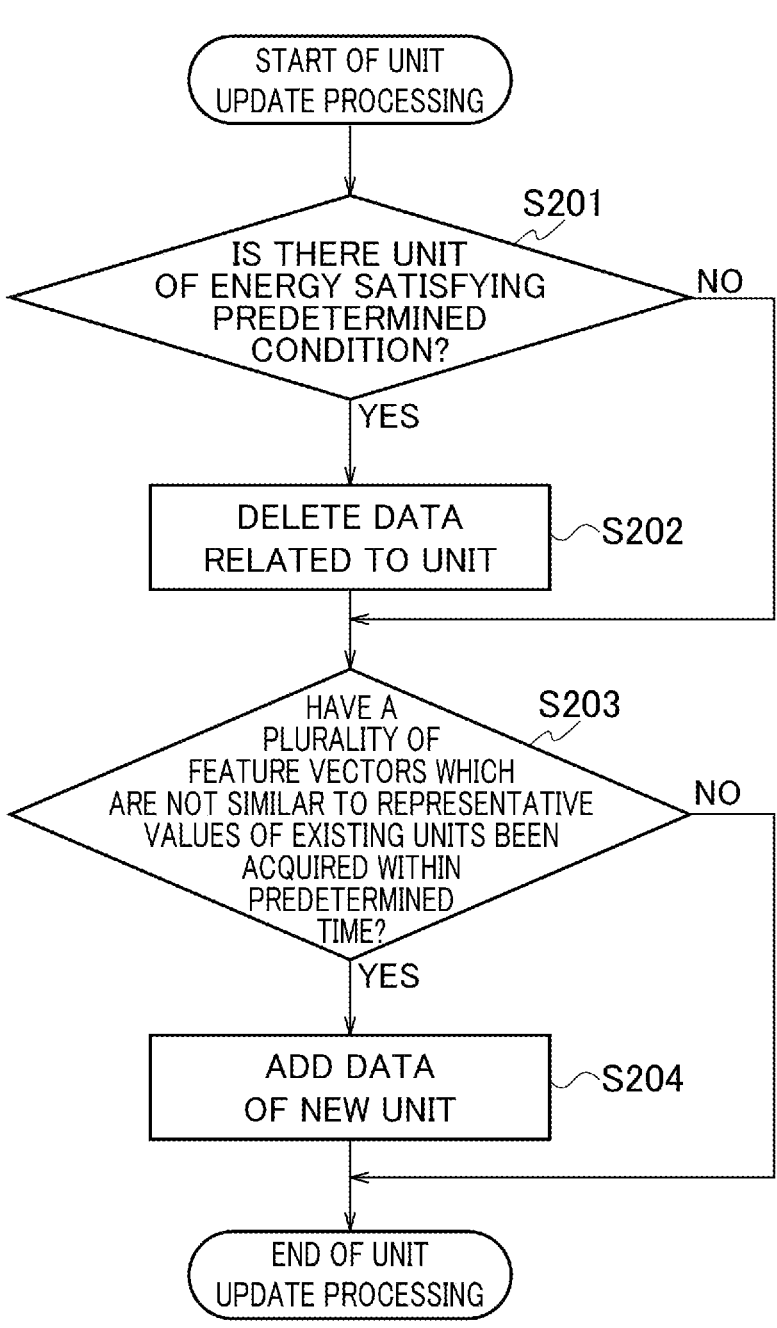
FIG. 10 is a flowchart illustrating the processing of a unit update unit.

With reference to FIG. 10, the unit update processing performed by the unit update unit 23 will be described. As an example of the processing, FIG. 10 illustrates a case, which is periodically performed, where a unit whose energy has attenuated at a predetermined timing is deleted, and a unit is added to a feature vector acquired from the previous processing.

In step S201, the unit update unit 23 determines whether or not there is a unit satisfying a predetermined condition due to the attenuation of energy. When there is a unit satisfying the predetermined condition, the unit update unit 23 deletes the data of the unit from the unit data 12 in step S202, and the processing proceeds to step S203. When there is no unit satisfying the predetermined condition, the processing proceeds to step S203.

In step S203, the unit update unit 23 determines whether or not there is a new unit to be added from the previous processing. Specifically, the unit update unit 23 determines whether or not a plurality of feature vectors, which are not similar to the representative values of the existing units and are similar to each other, have been acquired within a predetermined time. When there is no unit to be newly added, the unit update unit 23 ends the processing.

When there is a unit to be newly added, the unit update unit 23 adds the data of the newly added unit to the unit data 12 in step S204. The unit update unit 23 calculates a representative value and energy of the plurality of similar feature vectors acquired within a predetermined time. The unit update unit 23 inserts into the unit data 12, data associating an identifier of the new unit with the calculated representative value and energy.

When a plurality of units are newly added from the previous processing, the processing of step S204 is repeated for each unit.

The class update unit 24 updates the number of classes defined by the class data 13.

The class update unit 24 deletes a class identifier from the class data 13 when the data related to an identifier of a unit associated with the class identifier in the class data 13 is not found in the unit data 12. The data of each unit of the unit data 12 may be deleted by the unit update unit 23.

Then, the class update unit 24 determines whether or not the unit identifiers associated with each class are defined in the unit data 12. When they are not defined, the class update unit 24 deletes the unit identifiers not defined in the unit data 12 from the class data 13.

When data of all the units associated with a certain class are deleted from the unit data 12, the class update unit 24 also deletes data of the class in the class data 13. When one or more units associated with the class are defined in the unit data 12, the class update unit 24 maintains the data of the class.

When the unit update unit 23 defines a new unit, the class update unit 24 further determines a class to which the new unit belongs, and updates the class data 13.

When there is a unit having an attribute within a predetermined range of the attribute of a new unit generated by the unit update unit 23, the class update unit 24 adds the identifier of the new unit to the identifier of an existing class of the class data 13. Specifically, the class update 24 unit associates, in the class data 13, the identifier of the new unit with the identifier of the class associated with the identifier of the unit having the attribute within the predetermined range of the attribute of the new unit. This identifier of the new unit serves as the identifier of the unit included in the class. Meanwhile, when there is no unit having energy within a predetermined range of the attribute of the new unit, the class update unit 24 adds data in which an identifier of a new class is associated with the identifier of the new unit, to the class data 13.

The attribute of a unit is a representative value or energy. When the similarity between the representative value of a new unit and the representative value of an existing unit is high, the class update unit 24 associates the new unit with the class with which the existing unit having the high similarity is associated. When there is no existing unit having a high similarity, the class update unit 24 defines a new class and associates the new unit with the new class.

When energy is specified by the position and the amount of energy in the feature field, the class update unit 24 determines whether or not there is an existing unit whose position and amount of energy in the feature field are within a predetermined range of the energy of the new unit. When there is an existing unit within such a predetermined range, the new unit is also associated with the class with which the existing unit is associated. When there is no existing unit within a predetermined range, the class update unit 24 defines a new class and associates the new unit with the new class.

When the class update unit 24 defines a new class, it is typically the case where the user R attempts a new motion, and the myoelectric hand H expects a desired motion according to the new motion.

When an upper limit is set for the number of classes and the upper limit is exceeded by the addition of classes, the class update unit 24 may delete the data of the lowest energy class from the class data 13 and define the data of a new class in the class data 13. The low energy class is the case where the user R does not input a feature vector corresponding to the class, which means the use frequency is low.

Figure 11:
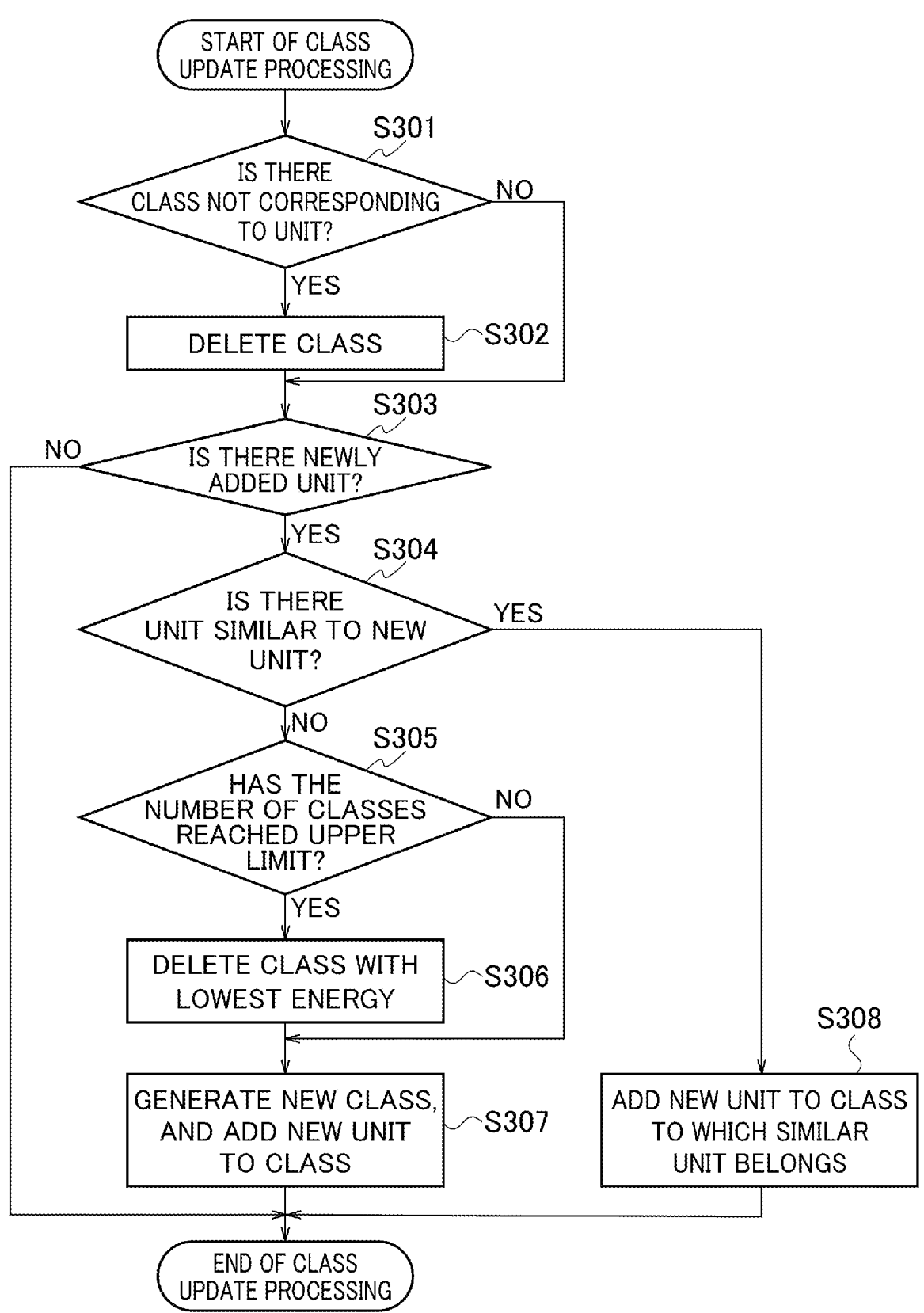
FIG. 11 is a flowchart illustrating the processing of a class attribute update unit.

With reference to FIG. 11, the class update processing performed by the class update unit 24 will be described.

First, in step S301, the class update unit 24 refers to the class data 13 and determines whether there is a class with which an identifier of a unit is not associated. When there is no class with which an identifier of a unit is not associated, the processing proceeds to step S303. When there is a class with which an identifier of a unit is not associated, the class update unit 24 deletes the data of the class from the class data 13 in step S302.

In step S303, the class update unit 24 determines whether or not there is a newly added unit from the previous processing. When there is no new unit, the processing ends as it is.

When there is a new unit, the class update unit 24 determines whether there is a unit having an attribute similar to the attribute of the new unit in step S304. When there is a unit having such a similar attribute, the class update unit 24 updates the class data 13 by associating the new unit with the class to which the unit having the similar attribute belongs in step S308, and ends the processing.

When there is no unit having a similar attribute, the class update unit 24 determines in step S305 whether or not the number of existing classes has reached the upper limit. If so, the class update unit 24 deletes the lowest energy class in step S306. In step S307, the class update unit 24 generates a new class, adds the new unit to the new class, updates class data 13, and ends the processing.

When a plurality of units have been newly added since the last processing, the processing of steps S304 to S307 is repeated for each new unit.

The motion update unit 25 updates the motion data 14 by associating an identifier of a motion corresponding to a class with a class identifier after the class update unit 24 has updated the class data 13. The motion update unit 25 associates motion identifiers with existing classes. A motion and a class may be associated with each other in consideration of the progress of processing so far. For example, a motion which is associated with a deleted class may be associated with a newly generated class. Alternatively, a motion and a may be randomly associated without considering the progress of processing.

The motion update unit 25 randomly changes an identifier of a motion corresponding to a class. When the association made after the random change is easily used by the user R, the association is continuously used. The continual use of the association means that a feature vector corresponding to the class is continuously input, that is to say, the user R causes a contraction of the muscle cells leading to the feature vector corresponding to the class, in expectation of the motion of the myoelectric hand H associated with the class. The class is maintained because the energy of such a class increases. Meanwhile, when the user R finds it difficult to use the association made after the random change, the energy of the class continues to attenuate and the class is deleted.

In a case where the motion update unit 25 attempts to change the association between an identifier of a motion and a class, the motion update unit 25 changes the motion of the identifier of the class to be changed when the motion of the identifier of the class to be changed is the same as the motion of the identifier of another class and the energy of the class to be changed is greater than the energy of the other class. In addition, the motion update unit 25 does not change the association when the motion of the identifier of the class to be changed is the same as the motion of the identifier of another class and the energy of the class to be changed is smaller than the energy of the other class.

In the embodiment of the present invention, when changing the association between a class and a motion at random, the motion update unit 25 determines whether or not the association should be changed in consideration of the usage situation of the user R. For example, an attempt is made to change the motion identifier A1 to the motion identifier A2 in the class ω1; however, the class ω2 has already been assigned to the motion identifier A2. In this case, the motion update unit 25 compares the energy of the class ω1 with the energy of the class ω2, and assigns the class identifier having the higher energy to the motion identifier A2.

In the embodiment of the present invention, the energy of the class increases with an input of a feature vector, and attenuates as time elapses. Since high energy means that a feature vector corresponding to a class is frequently input, the user R frequently uses the class. The motion update unit 25 preferentially assigns an identifier of a motion to a higher energy class in order to maintain such continuity. An identifier of a motion may be newly assigned to a lower energy class at random, or an identifier of a motion already assigned to a higher energy class may be assigned thereto.

In this way, the motion of the myoelectric hand H is associated with the class used by the user R, and the association is also changed at random, and thus the association between the class and the motion is learned. The motion update unit 25 can appropriately associate a motion in accordance with the usage situation of the user R even when the usage method of the user R changes.

When the acquisition unit 21 acquires a feature vector, the instruction output unit 26 specifies the class identifier including the unit to which the acquired feature vector belongs, refers to the motion data 14, and outputs instruction signal corresponding the specified class identifier. The instruction signal input to the myoelectric hand H, and the myoelectric hand H is activated according to the input instruction signal.

The instruction output unit 26 converts the myoelectric potential according to the intention of the user R into a motion of the myoelectric hand H, and can activate the myoelectric hand H according to the intention of the user R.

The conversion device 1 according to the embodiment of the present invention associates the instruction signal for the myoelectric hand H with the class generated from the myoelectric potential, and thus the class is maintained when the association is correct, and the class is eliminated when the association is incorrect. Accordingly, the myoelectric potential and the instruction signal can be correctly associated with each other even when there is no teacher data.

Thus, the conversion device 1 can learn the association between a myoelectric potential and a motion of the myoelectric hand H without using such teacher data.

FIRST MODIFICATION

In the embodiment of the present invention, a feature vector corresponding to the myoelectric potential input by the user R is associated with a unit, the unit is associated with a class, and the class is associated with an identifier of a motion, and thus the myoelectric potential input by the user R is converted into a motion signal for the myoelectric hand H. In the first modification, a description will be given regarding another method for converting the myoelectric potential input by the user R into a motion signal for the myoelectric hand H. In the first modification, a feature vector corresponding to the myoelectric potential input by the user R is associated with a class without being associated with a unit, and the class is associated with an identifier of a motion, and thus the myoelectric potential input by the user R is converted into a motion signal for the myoelectric hand H.

Figure 12:
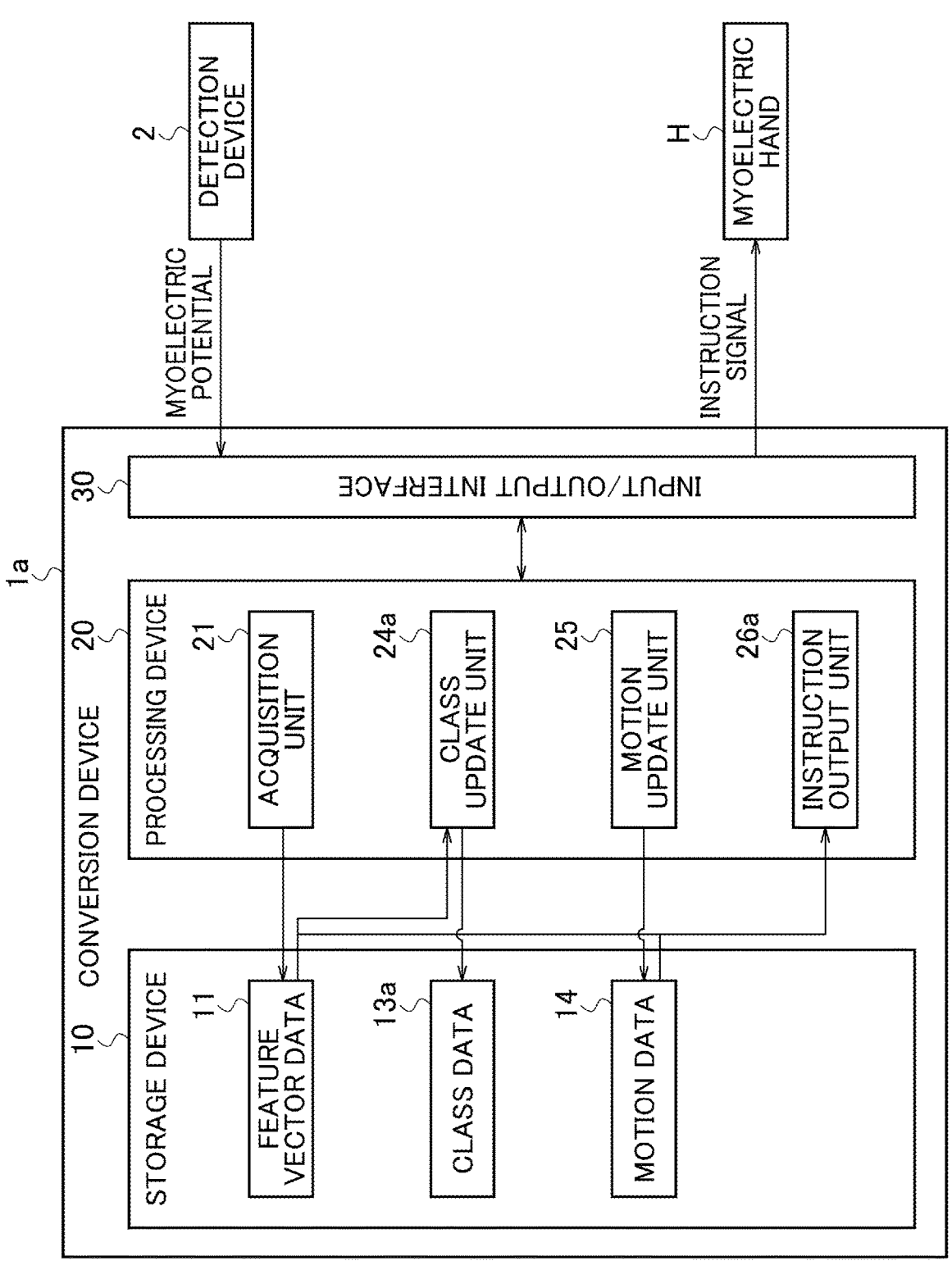
FIG. 12 is a diagram for explaining a hardware configuration and functional blocks of the conversion device according to a first modification.

With reference to FIG. 12, a conversion device 1a according to the first modification will be described. The conversion device 1a illustrated in FIG. 12 is different from the conversion device 1 illustrated in FIG. 5 in that the conversion device 1a does not include the unit data 12, the unit attribute update unit 22 and the unit update unit 23, in terms of the data structure for the class data 13a, in that the class update unit 24a refers to the feature vector data 11, and in terms of the processing of the instruction output unit 26a. The data structure for the feature vector data 11 and the motion data 14, and the processing of the acquisition unit 21 and the motion update unit 25 are the same as those of the conversion device 1 already described with reference to FIG. 5.

As illustrated in FIG. 13, the class data 13a associates an identifier of a class with the range of a feature vector included in the class, and the class energy. The range of the feature vector specifies the range of a feature vector belonging to the class. The energy is the energy of the class, and attenuates as time elapses and is amplified by the input of a feature vector within the range of the feature vector.

The class update unit 24a updates the class data 13a.

The class update unit 24a attenuates the energy of the class as time elapses. The class update unit 24a deletes data which is related to a class identifier satisfying a predetermined condition due to attenuation of energy, from the class data 13a. The predetermined condition is, for example, the total amount of energy becomes a predetermined value or less, the range influenced by energy becomes smaller than a predetermined region, or the value of energy at a predetermined position of the feature field becomes a predetermined value or less. That is, it is determined by the above predetermined condition that the amount of energy has reduced. The class update unit 24a attenuates the energy of each class of the class data 13a as time elapses. When there is a class satisfying the predetermined condition due to attenuation of energy, the class update unit 24a deletes the data of the class from the class data 13a.

The class update unit 24a also increases the energy of the class identifier corresponding to a new feature vector acquired by the acquisition unit 21. When the acquisition unit 21 acquires a new feature vector, the class update unit 24a compares the new feature vector with the ranges of the feature vectors of the class data 13a, and determines the class to which the new feature vector belongs. The class update unit 24a amplifies the energy of the class to which the new feature vector belongs.

When the acquisition unit 21 acquires a plurality of similar feature vectors outside the ranges of the feature vectors of the class data 13a within a predetermined time, the class update unit 24a adds, to the class data 13a, data as the identifier of a new class with the range of the feature vectors and energy of the new class.

Further, when the acquisition unit 21 acquires a feature vector, the instruction output unit 26a specifies the class identifier to which the acquired feature vector belongs. Here, the instruction output unit 26a refers to the class data 13a illustrated in FIG. 13, and specifies the class identifier associated with the range of the acquired feature vector. The instruction output unit 26a further refers to the motion data 14, and outputs an instruction signal corresponding to the specified class identifier.

Instead of defining the unit in the above manner, even in the case where the range and energy of the feature vector of each class are defined in the class data 13a without defining the unit in the above manner and the energy attenuates as time elapses and is amplified with the input of a new feature vector, the class can be defined according to the input state of the myoelectric potential.

Also in the first modification, the myoelectric hand H can be activated by a myoelectric potential by assigning an identifier of a motion of the myoelectric hand H to a class maintained by reflecting the input state of the myoelectric potential. Further, a better association relationship between a class identifier and an identifier of a motion can be found by randomly changing the class identifier and the motion identifier, and deleting the class according to the input state of the myoelectric potential of the user R after the random change. When a plurality of classes compete for an identifier of a motion due to the change, it becomes possible to continue a class which is easily used by the user R, by assigning the motion identifier to the class having higher energy, more specifically, to the class to which the myoelectric potential is continuously input.

Thus, the conversion device 1a can learn the association between the myoelectric potential and the motion of the myoelectric hand H without using teacher data.

SECOND MODIFICATION

In the embodiment and the first modification of the present invention, although the case of learning the association between the myoelectric potential and the motion of the myoelectric hand H without using teacher data has been described, the learning may be performed using teacher data.

A conversion device 1b (not illustrated) according to the second modification generates a classifier in which the association between a myoelectric potential and a motion (class) of the myoelectric hand H is learned by referring to learning data serving as teacher data, and outputs the motion (class) of the myoelectric hand H from the input myoelectric potential by using the generated classifier. In a learning phase of the classifier, the motion of the myoelectric hand H is not associated with a myoelectric potential itself, but with a unit which is a set of myoelectric potentials or a representative value of the myoelectric potentials in the unit. In an identification phase of the classifier, a myoelectric potential acquired by the user R using the myoelectric hand H is input, and the motion of the myoelectric hand H corresponding to the input myoelectric potential is output. In the second modification, a description will be given regarding the case in which a unit converted from a myoelectric potential is associated with a motion (class) of the myoelectric hand H as described in the embodiment of the present invention; however, a myoelectric potential may be associated with a motion (class) of the myoelectric hand H as described in the first modification. Further, since the output of the classifier is a class that is associated with one of the motions of the myoelectric hand H, the association between the motion and the class may be changed at random. As illustrated in the embodiment or the first modification of the present invention, the conversion device 1b may find a better association relationship between a class identifier and an identifier of a motion by randomly changing the class identifier and motion identifier, and deleting the class according to the input state of the myoelectric potential of the user R after the random change.

The conversion device 1b can generate a classifier at a frequency such as once a day. According to the knowledge of the inventors, the myoelectric potential has a time variation in which the myoelectric potential changes as time elapses doe to various factors such as a change in the position of the sensor caused by wearing or removing the myoelectric hand H, physiological factors such as fatigue or sweating, or a change in the gripping strategy. In particular, it is considered that a time variation of the myoelectric potential is likely to occur when the user R reattaches the myoelectric hand H at the start of a new day such as after getting up.

The conversion device 1b generates a classifier when the user R reattaches the myoelectric hand H. The learning data serving as the teacher data is data for associating a unit with a motion of the myoelectric hand H. The learning data is generated when the user R was wearing the myoelectric hand H, such as when wearing the myoelectric hand H on the previous day before reattaching the myoelectric hand H.

When the user R wears and activates the myoelectric hand H, the conversion device 1b can convert a unit converted from an input myoelectric potential a motion of the myoelectric hand H using the generated classifier. However, such a method may not be sufficient to cope with the time variation of the myoelectric potential.

Accordingly, after the user R wears and activates the myoelectric band H, the conversion device 1b acquires evaluation data when generating the classifier. The evaluation data is data of the myoelectric potentials acquired when the user R wears and activates the myoelectric hand H as a trial run in the case where the classifier is to be generated. The conversion device 1 compares the myoelectric potential of the units included in the learning data acquired on the previous day with the myoelectric potential of the evaluation data, and evaluates each unit included in the learning data.

The conversion device 1b sets the weight of a unit corresponding to the myoelectric potential included in the evaluation data to be high among the units included in the learning data. Further, the conversion device 1b sets the weight of a unit not corresponding to the myoelectric potential included in the evaluation data to be low among the units included in the learning data, or deletes a unit not corresponding to the myoelectric potential included in the evaluation data. The conversion device 1b generates one or more units with respect to a myoelectric potential not corresponding to the myoelectric potential of the unit included in the learning data among the myoelectric potentials included in the evaluation data, and inserts a generated unit into the learning data.

The conversion device 1b weights or deletes each unit of learning data acquired in the previous wearing of the myoelectric hand H based on the evaluation data acquired in the present test wearing of the myoelectric hand H, or adds a new unit reflecting the myoelectric potential in the wearing of the myoelectric hand H to the learning data, thereby generating learning data corresponding to the present wearing of the myoelectric hand H. Thus, it is possible to generate a classifier capable of following the time variation of the myoelectric potential.

The conversion device 1b may generate the classifier by means of online learning or offline learning.

Next, the classifier generated by the conversion device 1b is verified. In the verification, myoelectric potential data is used which is acquired when a healthy person wearing the myoelectric hand H repeatedly performs three trials which activate the myoelectric hand H with three target gripping forces in each of the two days. Here, the myoelectric hand H is activated by nine motions. These nine motions include rest, open palm, power grasp, precision grasp, lateral grasp, wrist flexion, wrist extension, wrist pronation, and wrist supination. The three target gripping forces are realized by randomly and visually feeding back the degree of force of the predetermined three levels to the person being tested, and adding the gripping forces thereto. In the verification, offline learning is used. In the classifier, a three-layer feed-forward type neural network is used.

The verification subject is data acquired by deleting a unit of myoelectric potential not included in the evaluation data from the previous learning data, and increasing the weight of the unit of myoelectric potential included in the evaluation data. As a function of the conversion device 1b, an addition of a unit to the learning data is also mentioned, but this function is not used in the verification. The comparison subject in the verification is the previous learning data itself. The conditions other than the learning data such as the number of times that learning is performed, learning rate, and parameters are the same between the verification subject and the comparison subject.

With reference to FIG. 14, a description will be given regarding the result of comparing the units of the evaluation data with the units of the learning data. The "data sets" illustrated in FIG. 14 and FIG. 15 (described later) are data acquired by the trial in which the myoelectric hand H is made to perform nine motions with three target gripping forces. This trial was repeated three times, and thus three data sets were validated. FIG. 14 illustrates that the conversion device 1b compares the units of the evaluation data and the units of the learning data, thereby deleting an average of 95.62% of the units, and leaving an average of 4.38% of the units and increasing the weights of these units.

This indicates that a smaller number of units of learning data required for identifying a motion of the myoelectric hand H are sufficient compared with the case where a person collects the learning data empirically. Since the number of units of learning data is small, the calculation time and the memory can be reduced. Since the myoelectric hand H is a robot to be worn by a human, it has volumetric and weight constraints. Accordingly it is suitable that the computational cost is low because the myoelectric hand H uses a small microcomputer. Since the conversion device 1b is used for deleting and scoring the units of learning data, it is not necessary to maintain the evaluation data itself, and it is necessary to maintain only the scores of the evaluation data in each unit required for scoring, and thus the memory capacity of the conversion device 1b can be reduced. It is expected that by narrowing down the number of units of learning data and reducing calculation time and the cost of memory capacity, the number of motions can be increased to realize more elaborate motions. In addition, it is expected that the amount of data can be increased to improve identification accuracy.

With reference to FIG. 15, a description will be given regarding the result of comparing the identification rates of verification subjects and those of comparison subjects. On average, each of the three data sets improved identification rates by 2.58% for the verification subjects over the comparison subjects. Generally, the identification rate improves as the number of data sets in the learning data increase, but the verification subjects acquire results having a higher identification rate than the comparison subjects for which data is not deleted, even though the data of the verification subjects is reduced by 95% or more. This indicates that units of useless learning data are deleted in the verification subjects, and appropriate weights are given to the remaining units not deleted.

However, according to the knowledge of the inventors, the identification rate in the case where the evaluation data and the learning data are acquired on the same day, in other words, the identification rate in the case where a time variation is not considered, is 95%. As illustrated in FIG. 15, since the identification rate in the verification subject is 82.86%, further improvement is expected in the future.

With reference to FIG. 16, the identification rates of each motion will be described in order to verify more detailed results. FIGS. 16(a) to 16(c) correspond to each of the three data sets of the verification subjects in FIG. 15. FIGS. 16(d)

to 16(*f*) correspond to each of the three data sets of the comparison subjects in FIG. 15.

In the respective tables illustrated in FIGS. 16(*a*) to 16(*f*), the rows indicate the motions which are actually performed, and the columns indicate the motions which are identified. The values in the row direction add up to 100%. Ideally, if all were correctly identified, 100% would be set for the cells in the diagonal direction, indicating that the row and column have the same behavior, and 0% would be set for the other cells.

In the example illustrated in FIG. 16, it can be seen that wrist supination (spn) is not identified in both the verification subject and the comparison subject. This is considered to be caused by the fact that wrist supination was learned as a different feature on the first and second days as a result of a large change in the application of force to wrist supination on the first and second days.

With respect to wrist supination (spn), the result of erroneous identification by the conversion device 1*b* is about half of that in each of open palm (opn) and wrist pronation (prn), and this result is not to be confused with other classes to be associated with the other motions due to a shortage of sensors, etc. As a result of learning wrist supination as a different feature on the first day and the second day, it is considered that the conversion device 1*b* misidentifies the motion of wrist supination as open palm or wrist pronation which is close to the motion of wrist supination. However, it is considered that the myoelectric potential features of wrist supination on the second day differ from those of open palm, wrist pronation, and wrist supination on the first day.

The above reason may be that there is no class corresponding to the myoelectric potential of wrist supination on the second day. The conversion device 1*b* generates a new class when there is a distribution different from any existing classes, but the unit generation function is not implemented in the verification. A new class can be assigned to wrist supination by implementing the unit generation function. Assuming that the identification rate for wrist supination is close to 100%, the overall identification rate will be about 95%, and thus it can be expected that the identification accuracy will be equivalent to that using the data on the same day.

FIGS. 15 and 16 illustrate the results of a classifier generated using learning data along with teaching data; however, it is considered that a good identification rate can be acquired even in a classifier generated without teaching data, such as with the conversion device illustrated in the embodiment of the present invention and the first modification. As illustrated in the embodiment of the present invention and the first and second modifications of the present invention, it is considered that a method in which a motion of the myoelectric hand H is associated with a class generated and maintained by reflecting the input state of the myoelectric potential is suitable for learning of the myoelectric hand H.

Figure 17:
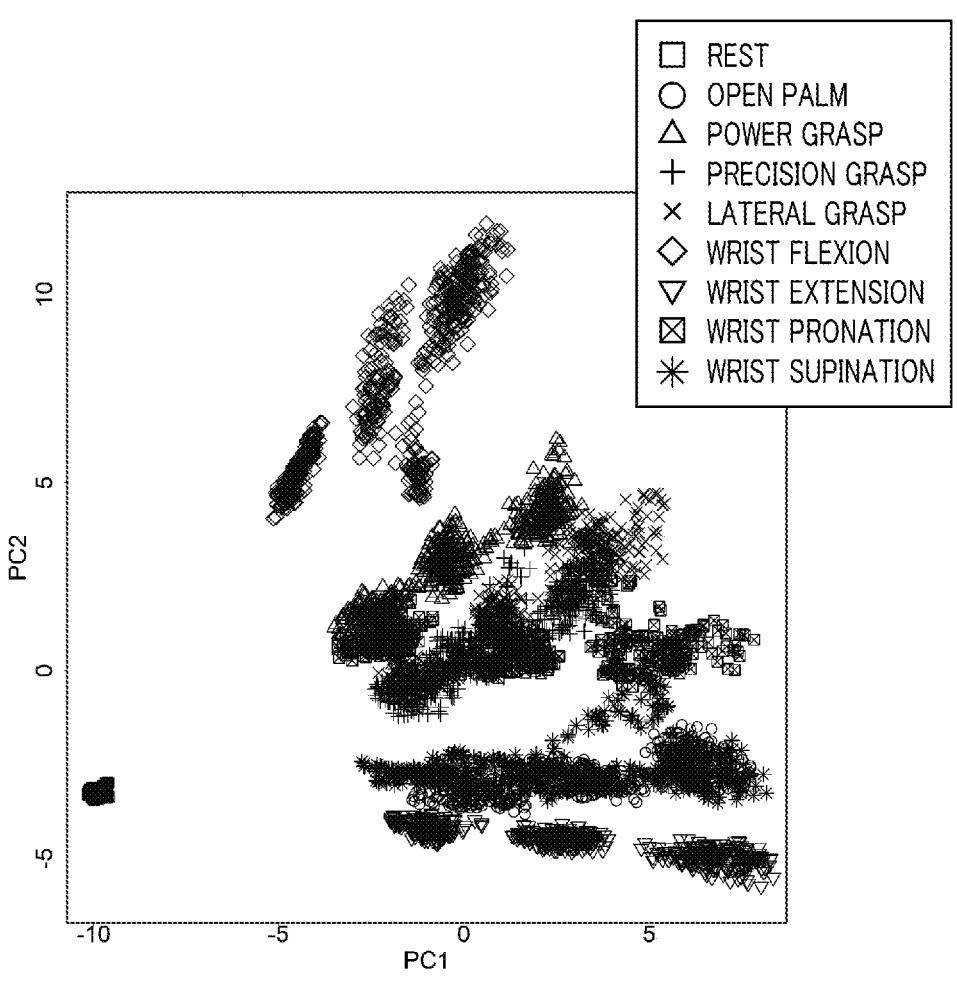
FIG. 17 illustrates myoelectric features when the myoelectric hand H is activated by three target gripping forces with nine motions.

With reference to FIGS. 17 and 18, an example of myoelectric features detected in the verification subject is illustrated. FIG. 17 illustrates myoelectric features when the myoelectric hand H having nine motions is activated with three target gripping forces. FIGS. 18(*a*), 18(*b*) and 18(*c*) illustrate myoelectric features when the myoelectric hand H having nine motions is activated with three target gripping forces. In FIGS. 17 and 18, the observed myoelectric features were 45 dimensions. Then, the number of dimensions was reduced by conducting principal component analysis, and the myoelectric features were projected in two dimensions.

The distribution of the myoelectric potential is formed radially for each motion in accordance with the degree of gripping force of three levels. In the graphs of FIGS. 17 and 18, it was confirmed that the myoelectric potential of the flexor muscle group was distributed on the upper side and the myoelectric potential of the extensor muscle group was distributed on the lower side.

The wrist supination that could not be identified in this verification was found to be close to the distribution in the open palm or wrist pronation that had been misidentified. This illustrates that even if the grasping strategy changes on the first and second days, such a distribution association does not change dramatically, and they are distributed close to each other. Accordingly, it has been suggested that it is possible to estimate which class (motion of the myoelectric hand H) should be assigned to a new distribution that is not learned yet, in consideration of the position of this kind of new distribution.

Other Embodiments

As described above, although an embodiment of the present invention and two modifications thereof have been described, it should not be understood that the statements and drawings forming part of this disclosure are intended to limit the invention. From this disclosure, various alternative embodiments, examples, and motional techniques become apparent to those skilled in the art.

For example, the conversion device according to the embodiment of the present invention may be configured on one piece of hardware as illustrated in FIG. 5, or may be configured on a plurality of pieces of hardware according to the function or the number of processes. It may also be implemented on an existing information processing system.

The flow of the processing illustrated in the embodiment of the present invention is merely an example, and the processing is not limited thereto.

Needless to say, the present invention includes various embodiments not described herein. Accordingly, the technical scope of the present invention is determined only by matters specifying the invention which may be reasonably claimed from the above description.

EXPLANATION OF THE REFERENCE NUMERALS

1 Conversion device
2 Detection device
5 Robot operation system
10 Storage device
11 Feature vector data
12 Unit data
13 Class data
20 Processing device
21 Acquisition unit
22 Unit attribute update unit
23 Unit update unit
24 Class update unit
25 Motion update unit
26 Instruction output unit
30 Input/output interface
H Myoelectric hand
R User

The invention claimed is:

1. A recording medium storing a conversion program for converting a biological signal generated in association with a human activity into an instruction signal for activating a robot, where executing of the conversion program causing one or more computers to perform operations comprising operations as:

an acquisition unit configured to sequentially acquire feature vectors for a biological signal;

a unit data storage unit configured to store unit data which associates an identifier of a unit, a representative value corresponding to a feature vector belonging to the unit, and energy corresponding to the feature vector belonging to the unit;

a class data storage unit configured to store class data that associates an identifier of a class with an identifier of a unit included in the class;

a unit attribute update unit configured to attenuate energy of the unit as time elapses, and specify a unit associated with a representative value approximating a new feature vector acquired by the acquisition unit, and update a representative value and energy of the specified unit based on the new feature vector;

a unit update unit configured to delete from the unit data, data related to an identifier of a unit satisfying a predetermined condition due to attenuation of the energy, and when the acquisition unit acquires a plurality of similar feature vectors outside a predetermined range of a representative value of the unit of the unit data within a predetermined time, add to the unit data, data associating an identifier of a new unit with a representative value and energy of the new unit;

a class update unit configured to, when there is another unit having an attribute within a predetermined range of an attribute of the new unit, add an identifier of the new unit in the class data as an identifier of a unit included in a class having the identifier of the other unit associated therewith, when there is no unit having an attribute within a predetermined range of an attribute of the new unit, add data associating an identifier of a new class with an identifier of the new unit to the class data, and when the unit data has no data related to an identifier of a unit associated with the class identifier in the class data, delete the class identifier from the class data;

a motion update unit configured to update motion data by associating, with an identifier of a class acquired after updating the class data, an identifier of a motion corresponding to the class; and an instruction output unit configured to, when the acquisition unit acquires a feature vector, specify an identifier of a class including a unit to which the acquired feature vector belongs, and output an instruction signal corresponding to the specified identifier of the class by referring to the motion data.

2. The recording medium according to claim 1, wherein the energy is expressed in terms of position and energy intensity in a feature field with parameters of the feature vector as axes, and operation as the unit attribute update unit comprises setting energy at a position corresponding to the feature vector in the feature field when the acquisition unit acquires the new feature vector, and updates the energy such that the set energy diffuses and attenuates as time elapses after the new feature vector is acquired.

3. The recording medium according to claim 1, wherein operation as the motion update unit comprises randomly changing an identifier of a motion corresponding to the class.

4. The recording medium according to claim 3, wherein
in response to the motion update unit attempting to change an association between an identifier of a motion and a class,
operation as the motion update unit comprises changing an identifier of a motion of a class to be changed when the motion identifier of the class to be changed is the same as an identifier of a motion of another class and energy of the class to be changed is greater than energy of the other class, and not changing the motion identifier of the class to be changed when energy of the class to be changed is smaller than energy of the other class.

5. A recording medium storing a conversion program for converting a biological signal generated in association with a human activity into an instruction signal for activating a robot, where executing of the conversion program causing one or more computers to perform operations comprising operations as:

an acquisition unit configured to sequentially acquire feature vectors for a biological signal;

a class data storage unit configured to store class data that associates an identifier of a class, a range of a feature vector included in the class, and energy of the class;

a class update unit configured to attenuate energy of the class as time elapses, delete from the class data, data related to an identifier of a class satisfying a predetermined condition due to attenuation of the energy, increase energy of an identifier of a class corresponding to a new feature vector acquired by the acquisition unit, and when the acquisition unit acquires a plurality of similar feature vectors outside a range of the feature vector of the class data within a predetermined time, add to the class data, data associating an identifier of a new class with a range of a feature vector of the new class and energy of the new class;

a motion update unit configured to update motion data by associating with, an identifier of a class acquired after updating the class data, an identifier of a motion corresponding to the class; and an instruction output unit configured to, when the acquisition unit acquires a feature vector, specify an identifier of a class to which the acquired feature vector belongs, and output an instruction signal corresponding to the specified identifier of the class by referring to the motion data.

\* \* \* \* \*